(12) United States Patent
Melkent et al.

(10) Patent No.: US 10,898,153 B2
(45) Date of Patent: Jan. 26, 2021

(54) MULTIPLE CANNULA IMAGE GUIDED TOOL FOR IMAGE GUIDED PROCEDURES

(75) Inventors: Anthony J. Melkent, Lafayette, CO (US); David M. Kahler, Earlysville, VA (US)

(73) Assignee: Medtronic Navigation, Inc., Louisville, CO (US)

( * ) Notice: Subject to any disclaimer, the term of this patent is extended or adjusted under 35 U.S.C. 154(b) by 1312 days.

(21) Appl. No.: 13/012,356

(22) Filed: Jan. 24, 2011

(65) Prior Publication Data
US 2011/0118593 A1 May 19, 2011

Related U.S. Application Data

(62) Division of application No. 10/801,906, filed on Mar. 16, 2004, now Pat. No. 7,881,770, which is a division
(Continued)

(51) Int. Cl.
*A61B 90/10* (2016.01)
*A61B 34/20* (2016.01)
(Continued)

(52) U.S. Cl.
CPC .............. *A61B 6/5235* (2013.01); *A61B 5/06* (2013.01); *A61B 5/064* (2013.01);
(Continued)

(58) Field of Classification Search
CPC ..... A61B 19/201; A61B 19/203; A61B 19/20; A61B 19/5244; A61B 19/22;
(Continued)

(56) References Cited

U.S. PATENT DOCUMENTS 1,576,781 A 3/1926 Phillips
1,735,726 A 11/1929 Bornhardt
(Continued)

FOREIGN PATENT DOCUMENTS

CA 964149 A1 3/1975
CA 2201877 * 4/1996 ............... A61B 6/03
(Continued)

OTHER PUBLICATIONS

"Prestige Cervical Disc System Surgical Technique", 12 pgs.
(Continued)

*Primary Examiner* — Kathleen S Holwerda
(74) *Attorney, Agent, or Firm* — Harness Dickey

(57) ABSTRACT

Apparatus and methods are disclosed for use within an image-guided surgical navigation system for facilitating the combined positioning and orientation of multiple surgical implements. A tool guide having multiple cannulas is tracked by a surgical navigation system in real time. Position data of the tool guide is registered and combined with pre-acquired images by the navigation computer. Concurrent graphical representations of the plurality of cannulas are superimposed over the images and displayed. The display allows the surgeon to place the tool guide into the patient's body and position and orient the plurality of cannulas which are then used to place each of the implements.

32 Claims, 9 Drawing Sheets

Related U.S. Application Data of application No. 09/795,126, filed on Mar. 1, 2001, now Pat. No. 6,725,080.

(60) Provisional application No. 60/186,200, filed on Mar. 1, 2000.

(51) Int. Cl.
  *A61B 6/00* (2006.01)
  *A61B 5/06* (2006.01)
  *A61B 17/17* (2006.01)
  *A61B 90/11* (2016.01)
  *A61B 5/00* (2006.01)
  *A61B 90/00* (2016.01)
  *A61B 34/00* (2016.01)
  *A61B 34/10* (2016.01)

(52) U.S. Cl.
  CPC .......... *A61B 17/1721* (2013.01); *A61B 34/20* (2016.02); *A61B 90/11* (2016.02); *A61B 5/0035* (2013.01); *A61B 5/743* (2013.01); *A61B 5/7425* (2013.01); *A61B 6/4441* (2013.01); *A61B 6/5247* (2013.01); *A61B 34/25* (2016.02); *A61B 2034/107* (2016.02); *A61B 2034/2055* (2016.02); *A61B 2034/2072* (2016.02); *A61B 2034/252* (2016.02); *A61B 2090/376* (2016.02); *A61B 2090/3983* (2016.02)

(58) Field of Classification Search
  CPC .......... A61B 2019/5483; A61B 17/162; A61B 17/17; A61B 19/52; A61B 1/32; A61B 17/02; A61B 17/0293; A61B 17/0206; A61B 1/303; A61B 17/1721; A61B 17/1714; A61B 17/1728; A61B 17/1796; A61B 17/1703; A61B 2017/3443; A61B 90/10; A61B 90/11; A61B 34/20; A61B 34/25
  USPC ........ 606/130; 600/424, 426, 427, 414, 417, 600/429
  See application file for complete search history.

(56) References Cited

U.S. PATENT DOCUMENTS

| | | |
|---|---|---|
| 2,182,390 A | 12/1939 | Reardon |
| 2,200,120 A * | 5/1940 | Nauth .............. 606/97 |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,847,157 A | 11/1974 | Caillouette et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,058,114 A | 11/1977 | Soldner |
| 4,117,337 A | 9/1978 | Staats |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,259,725 A | 3/1981 | Andrews et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,383,527 A * | 5/1983 | Asnis et al. ................... 606/96 |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,465,069 A | 8/1984 | Barbier et al. |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,686,997 A | 8/1987 | Oloff et al. |
| 4,688,037 A | 8/1987 | Krieg |
| 4,697,595 A | 10/1987 | Breyer et al. |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,747,400 A * | 5/1988 | Koeneman et al. .............. 606/54 |

(56) References Cited

U.S. PATENT DOCUMENTS

| | | |
|---|---|---|
| 4,750,487 A * | 6/1988 | Zanetti ............... 606/130 |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,907,577 A | 3/1990 | Wu |
| 4,911,153 A * | 3/1990 | Border ............... 606/98 |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,078,719 A * | 1/1992 | Schreiber ............... 606/87 |
| 5,079,699 A | 1/1992 | Tuy et al. |
| 5,080,662 A | 1/1992 | Paul |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,154,179 A | 10/1992 | Ratner |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,189,690 A | 2/1993 | Samuel |
| 5,190,059 A | 3/1993 | Fabian et al. |
| 5,193,106 A | 3/1993 | Desena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,207,753 A * | 5/1993 | Badrinath ............... 606/96 |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,250,055 A * | 10/1993 | Moore et al. ............... 606/148 |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,345,938 A | 9/1994 | Nishiki et al. |
| 5,353,795 A | 10/1994 | Souza et al. |
| 5,353,800 A | 10/1994 | Pohndorf et al. |

(56) References Cited

U.S. PATENT DOCUMENTS

| | | | | |
|---|---|---|---|---|
| 5,353,807 A | | 10/1994 | DeMarco | |
| 5,359,417 A | | 10/1994 | Muller et al. | |
| 5,368,030 A | | 11/1994 | Zinreich et al. | |
| 5,369,678 A | | 11/1994 | Chiu et al. | |
| 5,371,778 A | | 12/1994 | Yanof et al. | |
| 5,375,596 A | | 12/1994 | Twiss et al. | |
| 5,377,678 A | | 1/1995 | Dumoulin et al. | |
| 5,383,454 A | | 1/1995 | Bucholz | |
| 5,385,146 A | | 1/1995 | Goldreyer | |
| 5,385,148 A | | 1/1995 | Lesh et al. | |
| 5,386,828 A | | 2/1995 | Owens et al. | |
| 5,389,101 A | | 2/1995 | Heilbrun et al. | |
| 5,391,199 A | | 2/1995 | Ben-Haim | |
| 5,394,457 A | * | 2/1995 | Leibinger | A61B 6/12 378/162 |
| 5,394,875 A | | 3/1995 | Lewis et al. | |
| 5,397,329 A | | 3/1995 | Allen | |
| 5,398,684 A | | 3/1995 | Hardy | |
| 5,399,146 A | | 3/1995 | Nowacki et al. | |
| 5,400,384 A | | 3/1995 | Fernandes et al. | |
| D357,534 S | * | 4/1995 | Hayes | D24/140 |
| 5,402,801 A | | 4/1995 | Taylor | |
| 5,403,322 A | * | 4/1995 | Herzenberg et al. | 606/98 |
| 5,408,409 A | | 4/1995 | Glassman et al. | |
| 5,413,573 A | | 5/1995 | Koivukangas | |
| 5,417,210 A | | 5/1995 | Funda et al. | |
| 5,419,325 A | | 5/1995 | Dumoulin et al. | |
| 5,419,767 A | | 5/1995 | Eggers et al. | |
| D359,557 S | | 6/1995 | Hayes | |
| 5,423,334 A | | 6/1995 | Jordan | |
| 5,425,367 A | | 6/1995 | Shapiro et al. | |
| 5,425,382 A | | 6/1995 | Golden et al. | |
| 5,426,683 A | | 6/1995 | O'Farrell, Jr. et al. | |
| 5,426,687 A | | 6/1995 | Goodall et al. | |
| 5,427,097 A | | 6/1995 | Depp | |
| 5,429,132 A | | 7/1995 | Guy et al. | |
| 5,433,198 A | | 7/1995 | Desai | |
| RE35,025 E | | 8/1995 | Anderton | |
| 5,437,277 A | | 8/1995 | Dumoulin et al. | |
| 5,443,066 A | | 8/1995 | Dumoulin et al. | |
| 5,443,489 A | | 8/1995 | Ben-Haim | |
| 5,444,756 A | | 8/1995 | Pai et al. | |
| 5,445,144 A | | 8/1995 | Wodicka et al. | |
| 5,445,150 A | | 8/1995 | Dumoulin et al. | |
| 5,445,166 A | | 8/1995 | Taylor | |
| 5,446,548 A | | 8/1995 | Gerig et al. | |
| 5,447,154 A | | 9/1995 | Cinquin et al. | |
| 5,448,610 A | | 9/1995 | Yamamoto et al. | |
| 5,453,686 A | | 9/1995 | Anderson | |
| 5,456,718 A | | 10/1995 | Szymaitis | |
| 5,457,641 A | | 10/1995 | Zimmer et al. | |
| 5,458,718 A | | 10/1995 | Venkitachalam | |
| 5,464,446 A | | 11/1995 | Dreessen et al. | |
| 5,469,847 A | | 11/1995 | Zinreich et al. | |
| 5,474,559 A | * | 12/1995 | Bertin et al. | 606/89 |
| 5,478,341 A | | 12/1995 | Cook et al. | |
| 5,478,343 A | | 12/1995 | Ritter | |
| 5,480,422 A | | 1/1996 | Ben-Haim | |
| 5,480,439 A | | 1/1996 | Bisek et al. | |
| 5,483,961 A | | 1/1996 | Kelly et al. | |
| 5,484,437 A | | 1/1996 | Michelson | |
| 5,485,849 A | | 1/1996 | Panescu et al. | |
| 5,487,391 A | | 1/1996 | Panescu | |
| 5,487,729 A | | 1/1996 | Avellanet et al. | |
| 5,487,757 A | | 1/1996 | Truckai et al. | |
| 5,490,196 A | | 2/1996 | Rudich et al. | |
| 5,494,034 A | | 2/1996 | Schlondorff et al. | |
| 5,503,416 A | | 4/1996 | Aoki et al. | |
| 5,513,637 A | | 5/1996 | Twiss et al. | |
| 5,514,146 A | | 5/1996 | Lam et al. | |
| 5,515,160 A | | 5/1996 | Schulz et al. | |
| 5,517,990 A | | 5/1996 | Kalfas et al. | |
| 5,531,227 A | | 7/1996 | Schneider | |
| 5,531,520 A | | 7/1996 | Grimson et al. | |
| 5,531,751 A | | 7/1996 | Schultheiss et al. | |
| 5,542,938 A | | 8/1996 | Avellanet et al. | |
| 5,543,951 A | | 8/1996 | Moehrmann | |
| 5,546,940 A | | 8/1996 | Panescu et al. | |
| 5,546,949 A | | 8/1996 | Frazin et al. | |
| 5,546,951 A | | 8/1996 | Ben-Haim | |
| 5,551,429 A | | 9/1996 | Fitzpatrick et al. | |
| 5,558,091 A | | 9/1996 | Acker et al. | |
| 5,566,681 A | | 10/1996 | Manwaring et al. | |
| 5,568,384 A | | 10/1996 | Robb et al. | |
| 5,568,809 A | | 10/1996 | Ben-haim | |
| 5,571,109 A | | 11/1996 | Bertagnoli | |
| 5,572,999 A | * | 11/1996 | Funda et al. | 600/118 |
| 5,573,533 A | | 11/1996 | Strul | |
| 5,575,794 A | | 11/1996 | Walus et al. | |
| 5,575,798 A | | 11/1996 | Koutrouvelis | |
| 5,583,909 A | | 12/1996 | Hanover | |
| 5,588,430 A | | 12/1996 | Bova et al. | |
| 5,590,215 A | | 12/1996 | Allen | |
| 5,592,939 A | | 1/1997 | Martinelli | |
| 5,595,193 A | | 1/1997 | Walus et al. | |
| 5,596,228 A | | 1/1997 | Anderton et al. | |
| 5,600,330 A | | 2/1997 | Blood | |
| 5,603,318 A | | 2/1997 | Heilbrun et al. | |
| 5,606,980 A | | 3/1997 | Calhoun et al. | |
| 5,611,025 A | | 3/1997 | Lorensen et al. | |
| 5,617,462 A | | 4/1997 | Spratt | |
| 5,617,857 A | | 4/1997 | Chader et al. | |
| 5,619,261 A | | 4/1997 | Anderton | |
| 5,622,169 A | | 4/1997 | Golden et al. | |
| 5,622,170 A | | 4/1997 | Schulz | |
| 5,627,873 A | | 5/1997 | Hanover et al. | |
| 5,628,315 A | | 5/1997 | Vilsmeier et al. | |
| 5,630,431 A | | 5/1997 | Taylor | |
| 5,636,644 A | | 6/1997 | Hart et al. | |
| 5,637,112 A | * | 6/1997 | Moore et al. | 606/148 |
| 5,638,819 A | | 6/1997 | Manwaring et al. | |
| 5,640,170 A | | 6/1997 | Anderson | |
| 5,642,395 A | | 6/1997 | Anderton et al. | |
| 5,643,268 A | | 7/1997 | Vilsmeier et al. | |
| 5,645,065 A | | 7/1997 | Shapiro et al. | |
| 5,646,524 A | | 7/1997 | Gilboa | |
| 5,647,361 A | | 7/1997 | Damadian | |
| 5,649,946 A | * | 7/1997 | Bramlet | 606/167 |
| 5,651,047 A | | 7/1997 | Moorman et al. | |
| 5,662,111 A | | 9/1997 | Cosman | |
| 5,664,001 A | | 9/1997 | Tachibana et al. | |
| 5,665,095 A | * | 9/1997 | Jacobson | A61B 19/201 604/116 |
| 5,669,915 A | * | 9/1997 | Caspar et al. | 606/96 |
| 5,674,296 A | | 10/1997 | Bryan et al. | |
| 5,676,673 A | | 10/1997 | Ferre et al. | |
| 5,681,260 A | | 10/1997 | Ueda et al. | |
| 5,682,886 A | | 11/1997 | Delp et al. | |
| 5,682,890 A | | 11/1997 | Kormos et al. | |
| 5,690,108 A | | 11/1997 | Chakeres | |
| 5,694,945 A | | 12/1997 | Ben-Haim | |
| 5,695,500 A | * | 12/1997 | Taylor et al. | 606/130 |
| 5,695,501 A | | 12/1997 | Carol et al. | |
| 5,697,377 A | | 12/1997 | Wittkampf | |
| 5,697,939 A | * | 12/1997 | Kubota et al. | 606/130 |
| 5,702,406 A | | 12/1997 | Vilsmeier et al. | |
| 5,711,299 A | | 1/1998 | Manwaring et al. | |
| 5,713,946 A | | 2/1998 | Ben-Haim | |
| 5,715,822 A | | 2/1998 | Watkins et al. | |
| 5,715,836 A | | 2/1998 | Kliegis et al. | |
| 5,718,241 A | | 2/1998 | Ben-Haim et al. | |
| 5,727,552 A | | 3/1998 | Ryan | |
| 5,727,553 A | | 3/1998 | Saad | |
| 5,729,129 A | | 3/1998 | Acker | |
| 5,730,129 A | | 3/1998 | Darrow et al. | |
| 5,730,130 A | | 3/1998 | Fitzpatrick et al. | |
| 5,732,703 A | | 3/1998 | Kalfas et al. | |
| 5,735,278 A | | 4/1998 | Hoult et al. | |
| 5,738,096 A | | 4/1998 | Ben-Haim | |
| 5,740,802 A | | 4/1998 | Nafis et al. | |
| 5,741,214 A | | 4/1998 | Ouchi et al. | |
| 5,742,394 A | | 4/1998 | Hansen | |
| 5,744,953 A | | 4/1998 | Hansen | |
| 5,746,763 A | * | 5/1998 | Benderev et al. | 606/193 |

(56) References Cited

U.S. PATENT DOCUMENTS

| | | |
|---|---|---|
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,752,962 A | 5/1998 | D'Urso et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,762,629 A * | 6/1998 | Kambin .................. 604/164.11 |
| 5,767,669 A | 6/1998 | Hansen et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,772,661 A | 6/1998 | Michelson |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,712 A | 9/1998 | Dunn |
| 5,810,728 A | 9/1998 | Kuhn |
| 5,810,735 A | 9/1998 | Halperin et al. |
| 5,817,106 A | 10/1998 | Real |
| 5,820,553 A | 10/1998 | Hughes |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,833,627 A | 11/1998 | Shmulewitz et al. |
| 5,834,759 A | 11/1998 | Glossop |
| 5,836,950 A * | 11/1998 | Hansson ..................... 606/65 |
| 5,836,954 A | 11/1998 | Heilbrun et al. |
| 5,840,024 A | 11/1998 | Taniguchi et al. |
| 5,840,025 A | 11/1998 | Ben-Haim |
| RE36,020 E * | 12/1998 | Moore et al. .................. 606/144 |
| 5,843,076 A | 12/1998 | Webster, Jr. et al. |
| 5,848,967 A | 12/1998 | Cosman |
| 5,851,183 A | 12/1998 | Bucholz |
| 5,851,207 A | 12/1998 | Cesarone |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A * | 2/1999 | Warner et al. .................. 606/130 |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,150 A * | 4/1999 | Chan ..................... 606/96 |
| 5,891,157 A | 4/1999 | Day et al. |
| 5,895,389 A * | 4/1999 | Schenk et al. .................. 606/96 |
| 5,897,529 A | 4/1999 | Ponzi |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,938,603 A | 8/1999 | Ponzi |
| 5,938,694 A | 8/1999 | Jaraczewski et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,957,844 A | 9/1999 | Dekel et al. |
| 5,964,757 A | 10/1999 | Ponzi |
| 5,964,796 A | 10/1999 | Imran |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,145 A * | 11/1999 | Kennefick, III .................. 606/80 |
| 5,976,156 A | 11/1999 | Taylor et al. |
| 5,980,535 A * | 11/1999 | Barnett .............. A61B 17/3403 600/407 |
| 5,983,126 A | 11/1999 | Wittkampf |
| 5,984,930 A | 11/1999 | Maciunas et al. |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,021,342 A | 2/2000 | Brabrand |
| 6,021,343 A * | 2/2000 | Foley et al. .................. 600/429 |
| 6,024,695 A | 2/2000 | Taylor et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,066,142 A * | 5/2000 | Serbousek et al. ............. 606/96 |
| 6,071,288 A | 6/2000 | Carol et al. |
| 6,073,043 A | 6/2000 | Schneider |
| 6,076,008 A | 6/2000 | Bucholz |
| 6,095,975 A | 8/2000 | Silvern |
| 6,096,050 A | 8/2000 | Audette |
| 6,104,944 A | 8/2000 | Martinelli |
| 6,117,143 A * | 9/2000 | Hynes et al. .................. 606/130 |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,149,622 A | 11/2000 | Marie |
| 6,156,067 A | 12/2000 | Bryan et al. |
| 6,161,032 A | 12/2000 | Acker |
| 6,165,181 A | 12/2000 | Heilbrun et al. |
| 6,167,292 A | 12/2000 | Badano et al. |
| 6,167,296 A | 12/2000 | Shahidi |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,194,639 B1 | 2/2001 | Botella et al. |
| 6,201,387 B1 | 3/2001 | Govari |
| 6,203,497 B1 | 3/2001 | Dekel et al. |
| 6,211,666 B1 | 4/2001 | Acker |
| 6,223,067 B1 | 4/2001 | Vilsmeier et al. |
| 6,226,548 B1 * | 5/2001 | Foley et al. .................. 600/426 |
| 6,233,476 B1 | 5/2001 | Strommer et al. |
| 6,235,038 B1 * | 5/2001 | Hunter et al. .................. 606/130 |
| 6,236,875 B1 * | 5/2001 | Bucholz et al. .............. 600/407 |
| 6,246,231 B1 | 6/2001 | Ashe |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,314,310 B1 | 11/2001 | Ben-Haim et al. |

(56) References Cited

U.S. PATENT DOCUMENTS

| | | | |
|---|---|---|---|
| 6,317,616 B1* | 11/2001 | Glossop | 600/407 |
| 6,332,089 B1 | 12/2001 | Acker et al. | |
| 6,333,971 B2* | 12/2001 | McCrory | A61K 49/0409 |
| | | | 378/162 |
| 6,340,363 B1 | 1/2002 | Bolger et al. | |
| 6,341,231 B1 | 1/2002 | Ferre et al. | |
| 6,347,240 B1 | 2/2002 | Foley et al. | |
| 6,348,058 B1 | 2/2002 | Melkent et al. | |
| 6,351,659 B1 | 2/2002 | Vilsmeier | |
| 6,381,485 B1* | 4/2002 | Hunter | G06T 3/0068 |
| | | | 324/244 |
| 6,402,762 B2* | 6/2002 | Hunter et al. | 606/130 |
| 6,424,856 B1 | 7/2002 | Vilsmeier et al. | |
| 6,427,314 B1 | 8/2002 | Acker | |
| 6,428,541 B1* | 8/2002 | Boyd et al. | 606/86 A |
| 6,428,547 B1 | 8/2002 | Vilsmeier et al. | |
| 6,434,415 B1* | 8/2002 | Foley et al. | 600/425 |
| 6,437,567 B1 | 8/2002 | Schenck et al. | |
| 6,445,943 B1 | 9/2002 | Ferre et al. | |
| 6,470,207 B1 | 10/2002 | Simon et al. | |
| 6,474,341 B1 | 11/2002 | Hunter et al. | |
| 6,477,400 B1 | 11/2002 | Barrick | |
| 6,478,802 B2 | 11/2002 | Kienzle, III et al. | |
| 6,484,049 B1 | 11/2002 | Seeley et al. | |
| 6,490,467 B1* | 12/2002 | Bucholz et al. | 600/407 |
| 6,490,475 B1 | 12/2002 | Seeley et al. | |
| 6,491,699 B1 | 12/2002 | Henderson et al. | |
| 6,493,573 B1 | 12/2002 | Martinelli et al. | |
| 6,498,944 B1 | 12/2002 | Ben-Haim et al. | |
| 6,499,488 B1 | 12/2002 | Hunter et al. | |
| 6,516,046 B1 | 2/2003 | Frohlich et al. | |
| 6,527,443 B1 | 3/2003 | Vilsmeier et al. | |
| 6,537,232 B1* | 3/2003 | Kucharczyk et al. | 600/561 |
| 6,551,325 B2 | 4/2003 | Neubauer et al. | |
| 6,584,174 B2 | 6/2003 | Schubert et al. | |
| 6,609,022 B2 | 8/2003 | Vilsmeier et al. | |
| 6,611,700 B1 | 8/2003 | Vilsmeier et al. | |
| 6,640,128 B2 | 10/2003 | Vilsmeier et al. | |
| 6,675,040 B1* | 1/2004 | Cosman | 600/427 |
| 6,694,162 B2 | 2/2004 | Hartlep | |
| 6,701,179 B1 | 3/2004 | Martinelli et al. | |
| 6,725,080 B2 | 4/2004 | Melkent et al. | |
| 7,139,418 B2 | 11/2006 | Abovitz et al. | |
| 7,881,770 B2 | 2/2011 | Melkent et al. | |
| 2001/0007918 A1 | 7/2001 | Vilsmeier et al. | |
| 2002/0095081 A1 | 7/2002 | Vilsmeier et al. | |
| 2002/0198451 A1 | 12/2002 | Carson | |
| 2003/0181918 A1 | 9/2003 | Smothers et al. | |
| 2004/0024309 A1 | 2/2004 | Ferre et al. | |
| 2005/0256455 A1 | 11/2005 | Weststrate et al. | |

FOREIGN PATENT DOCUMENTS

| | | |
|---|---|---|
| CA | 2201877 A1 | 4/1996 |
| DE | 3042343 A1 | 6/1982 |
| DE | 3508730 | 9/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 4432890 A1 | 3/1996 |
| DE | 19715202 A1 | 10/1998 |
| DE | 19751761 A1 | 10/1998 |
| DE | 19832296 | 2/1999 |
| DE | 19747427 A1 | 5/1999 |
| DE | 10085137 | 11/2002 |
| EP | 0062941 | 10/1982 |
| EP | 0119660 | 9/1984 |
| EP | 0155857 | 9/1985 |
| EP | 0319844 | 6/1989 |
| EP | 0326768 A2 | 8/1989 |
| EP | 0350996 A1 | 1/1990 |
| EP | 0359773 A1 | 3/1990 |
| EP | 0419729 A1 | 4/1991 |
| EP | 0427358 A1 | 5/1991 |
| EP | 0456103 | 11/1991 |
| EP | 0469966 A1 | 2/1992 |
| EP | 0501993 A1 | 9/1992 |
| EP | 0581704 | 2/1994 |
| EP | 0651968 | 5/1995 |
| EP | 0655138 | 5/1995 |
| EP | 0755660 A2 | 1/1997 |
| EP | 0894473 A2 | 2/1999 |
| EP | 0908146 | 4/1999 |
| EP | 0930046 A2 | 7/1999 |
| FR | 2417970 | 9/1979 |
| FR | 2618211 B1 | 11/1991 |
| GB | 0 755 660 A | 8/1956 |
| GB | 0 950 379 A | 2/1964 |
| GB | 2094590 | 9/1982 |
| GB | 2164856 | 4/1986 |
| JP | 62327 | 1/1983 |
| JP | 61-94639 A | 10/1984 |
| JP | 63240851 | 10/1988 |
| JP | 2765738 T | 4/1991 |
| JP | 3267054 | 11/1991 |
| WO | WO-8809151 | 12/1988 |
| WO | WO-8905123 A1 | 6/1989 |
| WO | WO-9005494 | 5/1990 |
| WO | WO-9103982 | 4/1991 |
| WO | WO-9104711 A1 | 4/1991 |
| WO | WO-9107726 A1 | 5/1991 |
| WO | WO-9203090 | 3/1992 |
| WO | WO-9206645 A1 | 4/1992 |
| WO | WO-9404938 A1 | 3/1994 |
| WO | WO-9423647 | 10/1994 |
| WO | WO-9424933 | 11/1994 |
| WO | WO-9507055 | 3/1995 |
| WO | WO-9611624 A2 | 4/1996 |
| WO | WO-9632059 | 10/1996 |
| WO | WO-9731581 A1 | 9/1997 |
| WO | WO-9736192 | 10/1997 |
| WO | WO-9740764 A2 | 11/1997 |
| WO | WO-9749453 | 12/1997 |
| WO | WO-9808554 | 3/1998 |
| WO | WO-9838908 | 9/1998 |
| WO | WO-9915097 | 4/1999 |
| WO | WO-9921498 | 5/1999 |
| WO | WO-9923956 | 5/1999 |
| WO | WO-9926549 | 6/1999 |
| WO | WO-9929253 | 6/1999 |
| WO | WO-9933406 | 7/1999 |
| WO | WO-9937208 | 7/1999 |
| WO | WO-9938449 | 8/1999 |
| WO | WO-99/27839 A9 | 10/1999 |
| WO | WO-9952094 | 10/1999 |
| WO | WO-9960939 | 12/1999 |
| WO | WO-0001316 | 1/2000 |
| WO | WO-0130437 | 5/2001 |

OTHER PUBLICATIONS

Adams et al., "Orientation Aid for Head and Neck Surgeons," Innov. Tech. Biol. Med., vol. 13, No. 4, 1992, pp. 409-424.

Adams et al., Computer-Assisted Surgery, IEEE Computer Graphics & Applications, pp. 43-51, (May 1990).

Barrick, E. Frederick, "Distal Locking Screw Insertion Using a Cannulated Drill Bit: Technical Note," Journal of Orthopaedic Trauma, vol. 7., No. 3, 1993, pp. 248-251.

Barrick, E. Frederick, et al. "Case Report Prophylactic Intramedullary Fixation of the Tibia for Stress Fracture in a Professional Athlete," Journal of Orthopaedic Trauma, vol. 6, No. 2, 1992, pp. 241-244.

Barrick, E. Frederick, et al., "Technical Difficulties With the Brooker-Wills Nail in Acute Fractures of the Femur," Journal of Orthopaedic Trauma, vol. 4, No. 2, 1990 Raven Press, Ltd., New York, pp. 144-150.

Batnitzky et al., "Three-Dimensinal Computer Reconstructions of Brain Lesions from Surface Contours Provided by Computed Tomog-

(56) References Cited

OTHER PUBLICATIONS raphy: A Prospectus," Neurosurgery, vol. 11, No. 1, Part 1, 1982, pp. 73-84.
Benzel, Edward, C., et al., "Magnetic Source Imaging: A Review of the Magnes System of Biomagnetic Technologies Incorporated," Neurosurgery, vol. 33, No. 2, pp. 252-259, Aug. 1993.
Bergstrom, Mats, et al., "Stereotaxic Computed Tomography," Am. J. Roentgenol, 127:167-170, 1976, pp. 167-170.
Bouazza-Marouf et al.; "Robotic-Assisted Internal Fixation of Femoral Fractures", IMECHE., pp. 51-58 (1995).
Brack, et al., "Accurate X-ray Based Navigation in Computer-Assisted Orthopedic Surgery," CAR '98, pp. 716-722.
BrainLAB advertising sheets, 26 pages unnumbered.
Brown, R., M.D., A Stereotactic Head Frame for Use with CT Body Scanners, Investigative Radiology .COPYRGT. J.B. Lippincott Company, pp. 300-304 (Jul.-Aug. 1979).
Bryan, "Bryan Cervical Disc System Single Level Surgical Technique", Spinal Dynamics, 2002, pp. 1-33.
Bucholz, Richard D., et al., "A Comparison of Sonic Digitizers Versus Light Emitting Diode-Based Localization," Interactive Image-Guided Neurosurgery, Chapter 16, pp. 179-220.
Bucholz, Richard D., et al., "Variables Affecting the Accuracy of Stereotactic Localization Using Computerized Tomography," J. Neurosurg., vol. 79, pp. 667-673, Nov. 1993.
Bucholz, Richard D., M.D., "Intraoperative Ultrasonic Brain Shift Monitor and Analysis," 2 pages unnumbered.
Bucholz, Richard D., M.D., et al., "Image-Guided Surgical Techniques for Infections and Trauma of the Central Nervous System," Neurosurgery Clinics of North America, vol. 7, No. 2, Apr. 1996, pp. 187-200.
Bucholz, Richard D., M.D., et al., "The Correction of Stereotactic Inaccuracy Caused by Brain Shift Using an Intraoperative Ultrasound Device," CVRMed-MRCAS'97, First Joint Conference Computer Vision, Virtual Reality and Robotics in Medicine and Medical Robotics and Computer-Assisted Surgery, Grenoble, France, Mar. 19-22, 1997 Proceedings, pp. 459-466.
Bucholz, Richard D.; Smith, Kurt R.; Henderson, Jaimie; McDurmont, Lee; Shulz, Dean; "Intraoperative Localization Using a Three Dimensional Optical Digitizer," SPIE vol. 1894, pp. 312-322.
Champleboux et al., "Accurate Calibration of Cameras and Range Imaging Sensors: the NPBS Method," IEEE International Conference on Robotics and Automation, Nice, France, May 1992.
Champleboux, "Utilisation de Fonctions Splines pour la Mise au Point D'un Capteur Tridimensionnel sans Contact," Quelques Applications Medicales, Jul. 1991.
Cinquin et al., "Computer Assisted Medical Interventions," International Advanced Robotics Programme, Sep. 1989, pp. 63-65.
Cinquin, et al., "Computer Assisted Medical Interventions," IEEE Engineering in Medicine and Biology vol. 14, No. 3 May/Jun. 1995, pp. 254-263.
Clarysse, Patrick, et al., "A Computer-Assisted System for 3-D Frameless Localization in Stereotaxic MRI," IEEE Transactions on Medical Imaging, vol. 10, No. 4, pp. 523-529. Dec. 1991.
Clinical Applications of Modern Imaging Technology, Jan. 17-19, 1993, vol. 1894, Los Angeles, CA; pp. 8-14; pp. 64-69; pp. 70-77; pp. 122-130; pp. 132-135; p. 148; pp. 149-160; pp. 187-199; pp. 206-215; pp. 216-228; pp. 229-247; pp. 248-259; pp. 260-277; pp. 279-291; pp. 292-299; pp. 300-311; pp. 312-322.
Cutting M.D. et al., Optical Tracking of Bone Fragments During Craniofacial Surgery, Second Annual International Symposium on Medical Robotics and Computer Assisted Surgery, pp. 221-225, (Nov. 1995).
Dever, Bill and S. James Zinreich, M.D., "OR Role Seen for 3-D Imaging," Radiology Today, 2 pages unnumbered, Feb. 1991.
Feldmar et al., "3D-2D Projective Registration of Free-Form Curves and Surfaces," Rapport de recherche (Inria Sophia Antipolis), 1994, pp. 1-44.
Foley et al., "Fundamentals of Interactive Computer Graphics," The Systems Programming Series, Chapter 7, Jul. 1984, pp. 245-266.

Foley, "The StealthStation: Three-Dimensional Image-Interactive Guidance for the Spine Surgeon," Spinal Frontiers, Apr. 1996, pp. 7-9.
Foley, Kevin T., et al., "Image-Guided Intraoperative Spinal Localization," Intraoperative Neuroprotection (1996) part 3 Monitoring Ch. 19, pp. 325-340.
Friets, et al., "A Frameless Stereotaxic Operating Microscope for Neurosurgery," IEEE Transactions on Biomedical Engineering, vol. 36, No. 6 (Jun. 1989), pp. 608, 617.
Gallen, Christopher C., et al., "Intracranial Neurosurgery Guided by Functional Imaging," Surg. Neurol., vol. 42, pp. 523-530, 1994.
Galloway, R.L., Jr. et al, Optical localization for interactive, image-guided neurosurgery, SPIE, vol. 2164, pp. 137-145 (undated.
Germano, Isabelle M., Kelly, Patrick J., "Instrumentation, Technique and Technology," Neurosurgery, vol. 37, No. 2, pp. 348-350, Aug. 1995.
Gildenberg et al., "Calculation of Stereotactic Coordinates from the Computed Tomographic Scan," Neurosurgery, vol. 10, No. 5, May 1982, pp. 580-586.
Gomez, Camilo R., et al., "Transcranial Doppler Ultrasound Following Closed Head Injury: Vasospasm or Vasoparalysis," Surg. Neurol., vol. 35, No. 1, pp. 30-35, Jan. 1991.
Gonzalez, "Digital Image Fundamentals," Digital Image processing, Second Edition, 1987, pp. 52-54.
Gottesfeld Brown et al., "Registration of Planar Film Radiographs with Computer Tomography," Proceedings of MMBIA, Jun. 1996, pp. 42-51.
Grimson, W. Eric L., et al., "Virtual-Reality Technology is Giving Surgeons the Equivalent of X-ray Vision, Helping Them to Remove Tumors More Effectively, to Minimize Surgical Wounds and to Avoid Damaging Critical Tissues," Scientific American, Jun. 1999, pp. 63-69.
Grimson, W.E.L., An Automatic Registration Method for Frameless Stereotaxy, Image Guided Surgery, and enhanced Reality Visualization, IEEE, pp. 430-436 (1994).
Gueziec et al., "Registration of Computed Tomography Data to a Surgical Robot Using Fluoroscopy: A Feasibility Study," Computer Science/Mathematics, Sep. 27, 1996, 6 pages.
Guthrie, B.L., Graphic-Interactive Cranial Surgery: The Operating Arm System, Handbook of Stereotaxy Using the CRW Apparatus, Chapter 13, pp. 193-211 (undated.
Hamadeh et al, "Kinematic Study of Lumbar Spine Using Functional Radiographies and 3D/2D Registration," TIMC UMR 5525—IMAG.
Hamadeh et al., "Automated 3-Dimensional Computed Tomographic and Fluorscopic Image Registration," Computer Aided Surgery (1998), 3:11-19.
Hamadeh, Ali, et al., "Towards Automatic Registration Between CT and X-ray Images: Cooperation Between 3D/2D Registration and 2D Edge Detection," pp. 39-46.
Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).
Hatch, "Reference-Display System for the Integration of CT Scanning and the Operating Microscope," Thesis, Thayer School of Engineering, Oct. 1984, pp. 1-189.
Hatch, J.F., et al., "Reference-Display System for the Integration of CT Scanning and the Operating Microscope," Proceedings of the Eleventh Annual Northeast Bioengineering Conference, Mar. 14-15, 1985, IEEE 1985, pp. 252-254.
Heilbrun, M. Peter, et al., "Preliminary Experience with Brown-Roberts-Wells (BRW) Computerized Tomography Stereotaxic Guidance System," J. Neurosurg., vol. 59, pp. 217-222, Aug. 1983.
Heilbrun, M. Peter, M.D., "Computed Tomography-Guided Stereotactic Systems," Clinical Neurosurgery, Chapter 31.
Heilbrun, M. Peter, M.D., "Progressive Technology Applications," Neurosurgery for the Third Millenium, Ch. 15, pp. 191-198.
Heilbrun, M. Peter, M.D., et al. "Stereotactic Localization and Guidance Using a Machine Vision Technique," Proceedings of the Meeting of the American Society for Stereotactic and Functional Neurosurgery, Pittsburgh, PA, Jun. 16-19, 1991 Stereotactic Functional Neurosurgery; vol. 58: pp. 94-98.

(56) References Cited

OTHER PUBLICATIONS

Henderson, Jaime M., et al., "An Accurate and Ergonomic Method of Registration for Image-Guided Neurosurgery," Computerized Medical Imaging and Graphics, vol. 18, No. 4, pp. 273-277, 1994.
Hoerenz, "The Operating Microscope I. Optical Principles, Illumination Systems, and Support Systems," Journal of Microsurgery, vol. 1, 1980, pp. 364-369.
Hofstetter, R., et al., "Fluoroscopy Based Surgical Navigation-Concept and Clinical Applications" CAR '97, Computer Assisted Radiology and Surgery, Proceedings of the 11th International Symposium and Exhibition Berlin, Jun. 25-28, 1997, pp. 956-960.
Horner, M.D., Neil B., et al., "A Comparison of CT-Stereotaxic Brain Biopsy Techniques," Investigative Radiology, vol. 19, No. 5, Sep.-Oct. 1984, pp. 367-373.
Hounsfield, "Computerized transverse axial scanning (tomography): Part 1. Description of system," British Journal of Radiology, vol. 46, No. 552, Dec. 1973, pp. 1016-1022.
Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.
Jacques et al., "Computerized three-dimensional stereotaxic removal of small central nervous system lesion in patients," J. Neurosurg., vol. 53, Dec. 1980, pp. 816-820.
Joskowicz, Leo, et al., "Computer-Aided Image-Guided Bone Fracture Surgery: Concept and Implementation" Proceedings of the 12th International Symposium and Exhibition, CAR '98, pp. 710-715.
Kall, B., The Impact of Computer and Imgaging Technology on Stereotactic Surgery, Proceedings of the Meeting of the American Society for Stereotactic and Functional Neurosurgery, pp. 10-22 (1987).
Kato, et al., "A Frameless, Armless Navigational System for Computer Assisted Neurosurgery," 74 J. Neurosurg, 845-49, 1991.
Kelly et al., "Computer-assisted stereotaxic laser resection of intra-axial brain neoplasms," Journal of Neurosurgery, vol. 64, Mar. 1986, pp. 427-439.
Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.
Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).
Kelly, P.J., Computer-Directed Stereotactic Resection of Brain Tumors, Neurologica Operative Atlas, vol. 1, No. 4, pp. 299-313 (1991).
Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).
Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).
Kim, W.S. et al., A Helmet Mounted Display for Telerobotics, IEEE, pp. 543-547 (1988).
Klimek, "Long-Term Experience with Different Types of Localization Systems in Skull-Base Surgery," Ear, Nose, and Throat Surgery, vol. 51, pp. 635-638.
Kosugi, Y., et al., an Articulated Neurosurgical Navigation System Using MRI and CT Images, IEEE Trans. on Biomed, Eng. vol. 35, No. 2, pp. 147-152 (Feb. 1988).
Krybus, W., et. al., "Navigation Support for Surgery by Means of Optical Position Detection," Proceedings of CAR '91, pp. 362-366.
Kwoh, Y.S., Ph.D., et al., A New Computerized Tomographic-Aided Robotic Stereotaxis System, Robotics Age, vol. 7, No. 6, pp. 17-22 (Jun. 1985).
Laitinen et al., "An Adapter for Computed Tomography-Guided, Stereotaxis," Surg. Neurol., 1985, pp. 559-566.
Laitinen, "Noninvasive multipurpose stereoadapter," Neurological Research, Jun. 1987, pp. 137-141.
Lavallee et al, "Matching 3-D Smooth Surfaces with their 2-D Projections using 3-D Distance Maps," SPIE, vol. 1570, Geometric Methods in Computer Vision, 1991, pp. 322-336.
Lavallee et al., "Computer Assisted Driving of a Needle into the Brain," Proceedings of the International Symposium CAR '89, Computer Assisted Radiology, 1989, pp. 416-420.
Lavallee et al., "Computer Assisted Interventionist Imaging: The Instance of Stereotactic Brain Surgery," North-Holland MEDINFO 89, Part 1, 1989, pp. 613-617.
Lavallee et al., "Matching of Medical Images for Computed and Robot Assisted Surgery," IEEE EMBS, Orlando, 1991.
Lavallee, "A New System for Computer Assisted Neurosurgery," IEEE Engineering in Medicine & Biology Society 11th Annual International Conference, 1989, 2 pages.
Lavallee, "VI Adaption de la Methodologie a Quelques Applications Cliniques," Chapitre VI, pp. 133-148.
Lavallee, et al., "Computer Assisted Medical Interventions," NATO ASI 1990, pp. 301-312, vol. F60.
Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).
Lavallee, S., et al., Computer Assisted Spine Surgery: A Technique for Accurate Transpedicular Screw Fixation using CT Data and a 3-D Optical Localizer, pp. 315-322.
Lavallee, Stephane, et al., "Image Guided Operating Robot: a Clinical Application in Stereotactic Neurosurgery," Proceedings of the 1992 IEEE International Conference on Robotics and Automation, Nice, France—May 1992, pp. 618-624.
Leavitt, Dennis D. Ph.D., et al., "Dynamic Field Shaping to Optimize Stereotactic Radiosurgery," Int. J. Radiation Oncology Biol. Phys., vol. 21, pp. 1247-1255.
Leksell et al., "Stereotaxis and Tomography—A Technical Note," ACTA Neurochirurgica, vol. 52, 1980, pp. 1-7.
Lemieux, L., et al., "A Patient-to-computed-tomography Image Registration Method Based on Digitally Reconstructed Radiographs," Medical Physics, vol. 21, No. 11, Nov. 1994, pp. 1749-1760.
Levin et al., "The Brain: Integrated Three-dimensional Display of MR and PET Images," Radiology, vol. 172, No. 3, Sep. 1989, pp. 783-789.
Marouf, K Bouazza, et al., "Robotic-assisted Internal Fixation of Femoral Fractures," Journal of Engineering in Medicine, vol. 209, 1995, pp. 51-58.
Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).
Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.
Mazier, et al., "Computer Assisted Interventionist Imaging: Application to the Vertebral Column Surgery," IEEE, vol. 12, No. 1, 1990, pp. 430-431.
McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).
Meloz, Philippe, M.D., et al., "Computer Assisted Spine Surgery," Clinical Orthopaedics and Related Research, No. 337, 1997, pp. 86-89.
Ng, W.S. et al., Robotic Surgery—A First-Hand Experience in Transurethral Resection of the Prostate Surgery, IEEE Eng. in Med. and Biology, pp. 120-125 (Mar. 1993).
Paul, et al., "Development of a Surgical Robot for Cementless Total Hip Arthroplasty," Clinical Orthopaedics, No. 285, Dec. 1992, pp. 57-66.
Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).
Pelizzari et al., No. 528—"Three Dimensional Correlation of PET, CT and MRI Images," The Journal of Nuclear Medicine, vol. 28, No. 4, Apr. 1987, p. 682.

(56) References Cited

OTHER PUBLICATIONS

Pelizzari, Charles A., et al., "Accurate Three-Dimensional Registration of CT, PET, and/or MR Images of the Brain," Journal of Computer Assisted Tomography, 13(1):20-26, Jan./Feb. 1989, pp. 20-26.
Penn, Richard D., et al., "Stereotactic Surgery with Image Processing of Computerized Tomographic Scans," Neurosurgery, vol. 3, No. 2, pp. 157-163, Sep./Oct. 1978.
Pixsys 3-D Digitizing Accessories, 2 unnumbered pages.
Potamianos et al., "Intra-Operative Imaging Guidance for Keyhole Surgery Methodology Calibration," First International Symposium on Medical Robotics and Computer Assisted Surgery, Sep. 22-24, 1994, pp. 98-104.
R. Phillips, et al., "Image Guided Orthopaedic Surgery Design and Analysis," Transactions of the Institute of Measurement and Control, vol. 17, No. 5, 1995, pp. 251-264.
Reinhardt et al., "CT-Guided 'Real Time' Stereotaxy," ACTA Neurochirurgica, 1989.
Reinhardt, H., et al., A Computer-Assisted Device for Intraoperative CT-Correlated Localization of Brain Tumors, pp. 51-58 (1988).
Reinhardt, H.F., "Neuronavigation: A Ten-Year Review," Neurosurgery, vol. 23, pp. 329-341.
Reinhardt, H.F., et al., "Sonic Stereometry in Microsurgical Procedures for Deep-Seated Brain Tumors and Vascular Malformations," Neurosurgery, vol. 32, No. 1, Jan. 1993, pp. 51-57.
Reinhardt, H.F.; Horstmann, G.A.; Gratzl, O.; "Mikrochirurgische Entfernung tiefliegender Gefa.beta.mi.beta.bildungen mit Hilfe der Sonar-Sterometrie" ("Microsurgical Removal of Deep-Seated Vascular Malformations Using Sonar Stereometry"),Ultraschall in Med. 12 (1991), pp. 80-84.
Roberts, M.D., David W., et al.; "A Frameless Stereotaxic Integration of Computerized Tomographic Imaging and the Operating Microscope," J. Neurosurg., vol. 65, pp, 545-549, Oct. 1986.
Rosenbaum et al., "Computerized Tomography Guided Stereotaxis: A New Approach," Applied Neurophysiology, vol. 43, No. 3-5, 1980, pp. 172-173.
Sautot, "Vissage Pediculaire Assiste Par Ordinateur," Sep. 20, 1994.
Schueler et al., "Correction of Image Intensifier Distortion for Three-Dimensional X-Ray Angiography," SPIE Medical Imaging 1995, vol. 2432, pp. 272-279.
Selvik et al., "A Roentgen Stereophotogrammetric System," Acta Radiologica Diagnosis, 1983, pp. 343-352.
Shelden et al., "Development of a computerized microsteroetaxic method for localization and removal of minute CNS lesions under direct 3-D vision," J. Neurosurg., vol. 52, 1980, pp. 21-27.
Simon, D.A., Accuracy Validation in Image-Guided Orthopaedic Surgery, Second Annual Intl. Symp. on Med. Rob. an Comp-Assisted surgery, MRCAS '95, pp. 185-192 (undated).
Smith, Kurt R., et al., "Multimodality Image Analysis and Display Methods for Improved Tumor Localization in Stereotactic Neurosurgery," Annual Conference of the IEEE Engineering in Medicine and Biology Society, vol. 13, No. 1, p. 210, 1991.
Smith, Kurt R., et al.; "Computer Methods for Improved Diagnostic Image Display Applied to Stereotactic Neurosurgery," Automedica, vol. 14, pp. 371-382, 1992.
Smith, Kurt R.; Frank, Kevin J.; Bucholz, Richard D.; "The Neurostation.TM.—A Highly Accurate, Minimally Invasive Solution to Frameless Stereotactic Neurosurgery," Computerized Medical Imaging and Graphics, vol. 18, No. 4, 1994, pp. 247-256.
Stereotactic one, "Affordable PC Based Graphics for Stereotactic Surgery," Stereotactic Image Systems, Inc., Salt Lake City, Utah, 6 pages unnumbered.
Tan, K., Ph.D., et al., A frameless stereotactic approach to neurosurgical planning based on retrospective patient-image registration, J Neurosurgy, vol. 79, pp. 296-303 (Aug. 1993).
The Laitinen Stereotactic System, E2-E6.
Thompson, et al., A System for Anatomical and Functional Mapping of the Human Thalamus, Computers and Biomedical Research, vol. 10, pp. 9-24 (1977).
Trobaugh, J.W., et al., Frameless Stereotactic Ultrasonography: Method and Applications, Computerized Medical Imaging and Graphics, vol. 18, No. 4, pp. 235-246 (1994).
Viant, W.J., et al., "A Computer Assisted Orthopaedic System for Distal Locking of Intramedullary Nails," pp. 86-91.
Von Hanwhr et al., Foreword, Computerized Medical Imaging and Graphics, vol. 18, No. 4, pp. 225-228, (Jul.-Aug. 1994).
Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).
Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.
Watanabe, "Neuronavigator," Igaku-no-Ayumi, vol. 137, No. 6, May 10, 1986, pp. 1-4.
Watanabe, E., M.D., et al., Open Surgery Assisted by the Neuronavigator, a Stereotactic, Articulated, Sensitive Arm, Neurosurgery, vol. 28, No. 6, pp. 792-800 (1991).
Weese et al., "An Approach to 2D/3D Registration of a Vertebra in 2D X-ray Fluoroscopies with 3D CT Images," pp. 119-128.
Weinstein, James N., D.O.; "Spinal Pedicle Fixation: Reliability and Validity of Roentgenogram-Based Assessment and Surgical Factors on Successful Screw Placement," Spine, vol. 13, No. 9, 1988, pp. 1012-1017.
Yeates, Andrew M.D., et al.; "Simplified and Accurate CT-Guided Needle Biopsy of Central Nervous System Lesions," Journal of Neurosurgery, vol. 57, No. 3, Sep. 1982, pp. 390-393.
C. Brack, et al., "Accurate X-Ray-Based Navigation in the Computer-Assisted Orthopedic Surgery," Proceedings of the 12th International Symposium and Exhibition, CAR '98, pp. 716-722.
Galloway, Jr., Robert L., et al., "Interactive Image-Guided Neurosurgery," IEEE Transactions on Biomedical Engineering, vol. 39, No. 12, pp. 1226-1231, Dec. 1992.
Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6,pp. 62-69 (Jun. 1999).
Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).
Heilbrun, M.P., Computed Tomography-Guided Stereotactic Systems, Clinical Neurosurgery, Chapter 31, pp. 564-581 (1983).
Simon, D.A.; O'Toole, R.V.; Blackwell, M.; Morgan, F.; DiGioia, A.M.; Kanade, T.; "Accuracy Validation in Image-Guided Orthopaedic Surgery," pp. 185-192.

* cited by examiner

MULTIPLE CANNULA IMAGE GUIDED TOOL FOR IMAGE GUIDED PROCEDURES

CROSS-REFERENCE TO RELATED APPLICATIONS

This application is a divisional of U.S. patent application Ser. No. 10/801,906 filed on Mar. 16, 2004, which is a divisional of U.S. patent application Ser. No. 09/795,126 filed Mar. 1, 2001, now U.S. Pat. No. 6,725,080 issued on Apr. 20, 2004, which claims the benefit of U.S. Provisional Application No. 60/186,200 filed on Mar. 1, 2000. The entire disclosures of each of the above applications are incorporated herein by reference.

BACKGROUND OF THE INVENTION

The present invention is directed generally to image-guided medical procedures, and more particularly, to instrumentation for the optimal placement of multiple surgical implements using image-based surgical guided navigation systems.

Many surgical procedures include a surgeon placing multiple implements within a patient's body. Some of these procedures dictate implement placement in a specific geometry to maximize the effectiveness of the treatment. Certain factors, such as the characteristics of the patient's anatomy, can also influence the desired relative placement of the multiple implements. Some procedures place the implements at a specified angle relative to each other, while others may use a parallel arrangement. One such procedure which utilizes a parallel configuration is the fixation of a femoral neck fracture. Typically, this type of fracture is stabilized utilizing three parallel cannulated screws. Each screw is placed perpendicularly to the fracture site and in such a manner that the distance between each screw is equal, thus forming an equilateral triangle. Parallel placement of the screws is desired so that the bones are properly pulled together. If the screws are not placed in such a parallel manner, shearing forces at the fracture site can prevent proper healing. Furthermore, the triangular screw arrangement increases the stability of the fracture fixation and prevents rotation between the bone fragments. Studies have suggested that three screws are an optimal number since additional implements provide no strength advantage and additional screw penetration increases risk. Femoral neck fracture stabilization using this method can be performed percutaneously while the patient is under regional anesthesia, thus reducing risk associated with more invasive procedures.

Traditional techniques to accurately position and orient implements have included the use of x-ray images to localize the position of the implement tool guide. Through the continuous acquisition of x-ray images during the medical procedure, real-time placement of the tool guide relative to the patient's anatomy can be displayed. More recently, fluoroscopically-based surgical navigation systems have been employed for tool guide positioning by tracking the tool and superimposing its representation onto pre-acquired images without requiring x-rays to be continually taken during the actual surgical procedure.

Current practice for multiple implement placement utilizing image-based surgical navigation systems typically employs tracked guides which contain a single cannula. As used herein, the term cannula refers to a tubular member having at least one hollow channel (i.e., lumen), for insertion in and/or placement adjacent to a patient's body. Such an instrument could be used to place implements in and/or adjacent to a patient by positioning the cannula in the region of interest, and then placing the implement in the region by means of the channel. As used herein, the term implement refers to a surgical tool or device for performing medical procedures. An implement could be a drill, a guide wire, or implants such as screws, nails, etc.

Those skilled in the art should recognize that there are many different types of cannulas and many different ways in which cannulas could be used. For example, a cannula could be rigid, semi-rigid, or flexible and could be configured in any number of different forms, such as a catheter, needle, endoscope, implement inserter, etc.

Utilizing a single cannula means the surgeon typically will position each implement individually. The procedure usually starts by attaching a reference tracking frame to the surgical anatomy. X-ray images are then taken utilizing a fluoroscopic imager which is also tracked by the navigation system. The surgeon then positions the tracked guide for the first implement with the aid of the navigational system display. Once the tool guide is properly positioned, the cannula is used to place the guide wire and subsequent implement into the desired anatomical site. The next implement is then placed relative to the first, and so on. In order for the surgeon to properly place the subsequent implement relative to the previous, new images are taken with the previous implement in place.

One difficulty of the current practice is in achieving relative accuracy of the implement placement. To achieve the desired relative implement geometry, the surgeon estimates each trajectory individually based upon the prior implements. Thus, the relative accuracy is based on the physician's estimate. Furthermore, each implement may involve generating a new set of images of the patient's anatomy before the subsequent implement can be placed, which can increase the time of the procedure and radiation exposure to both the patient and operating room personnel.

SUMMARY OF THE INVENTION

The present invention is directed generally to image guided medical procedures, and, particularly, medical procedures which utilize surgical implements. More specifically, the present invention is directed to an apparatus and method for the combined positioning of multiple implements, especially those that may be placed in a specific relative geometry.

As embodied and broadly described herein, certain aspects of the invention are directed to a multiple cannula tool guide for use in conjunction with image-guided surgical navigation systems.

In one aspect of the invention, an apparatus for use in image guided surgery is presented. The apparatus comprises: an instrument location system for detecting position, where the instrument location system includes a computer processor; a tool guide comprising a plurality of cannulas; and at least one trackable marker provided on the tool guide for detection by the instrument location system; a memory coupled to the computer processor stores: at least one pre-acquired image of a patient having an image space, and instructions, to be executed by the computer processor, to align the image space to a detector space, to track a three-dimensional position of the tool guide in the detector space, and to compute a projection of the tool guide into the at least one pre-acquired image.

In another aspect of the invention, an apparatus for the placement of surgical implements is presented. The apparatus comprises: a plurality of cannulas coupled to a fixture, where at least one trackable marker associated with the cannulas; a plurality of surgical implement receivers provided on the fixture for receiving surgical implements; and at least one of the plurality of receivers being substantially coaxially aligned with a respective one of the plurality of cannulas.

In another aspect of the invention, an apparatus for the placement of surgical implements, is presented. The apparatus comprises: a plurality of cannulas, where at least one of the plurality of cannulas is adjustable to vary its length; a fixture coupled to the plurality of cannulas, where the fixture can accommodate at least one of the plurality of cannulas being individually adjustable to vary at least one of its angular position; and at least one trackable marker associated with the cannulas.

In another aspect of the invention, a method for guiding a medical instrument for use in image guided surgery is presented. The method comprises: providing at least one pre-acquired image of a patient, the at least one image having an image space; aligning the image space and a detector space; tracking a three-dimensional position of a tool guide in the detector space, using at least one trackable marker provided on the tool guide, where the tool guide includes a plurality of cannulas; and relating the position of the cannulas with the at least one pre-acquired image.

Combined positioning of surgical implements may mitigate the amount of estimation a surgeon performs when positioning implements individually. This can result in improved placement efficiency and reduced surgical procedure time. Additional savings in time may also be realized by reducing the number of pre-acquired images generated during a surgical procedure.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION

Reference will now be made in detail to the present preferred embodiments of the invention, examples of which are illustrated in the accompanying drawings. Wherever possible, the same reference numbers will be used throughout the drawings to refer to the same or like parts.

Figure 1:
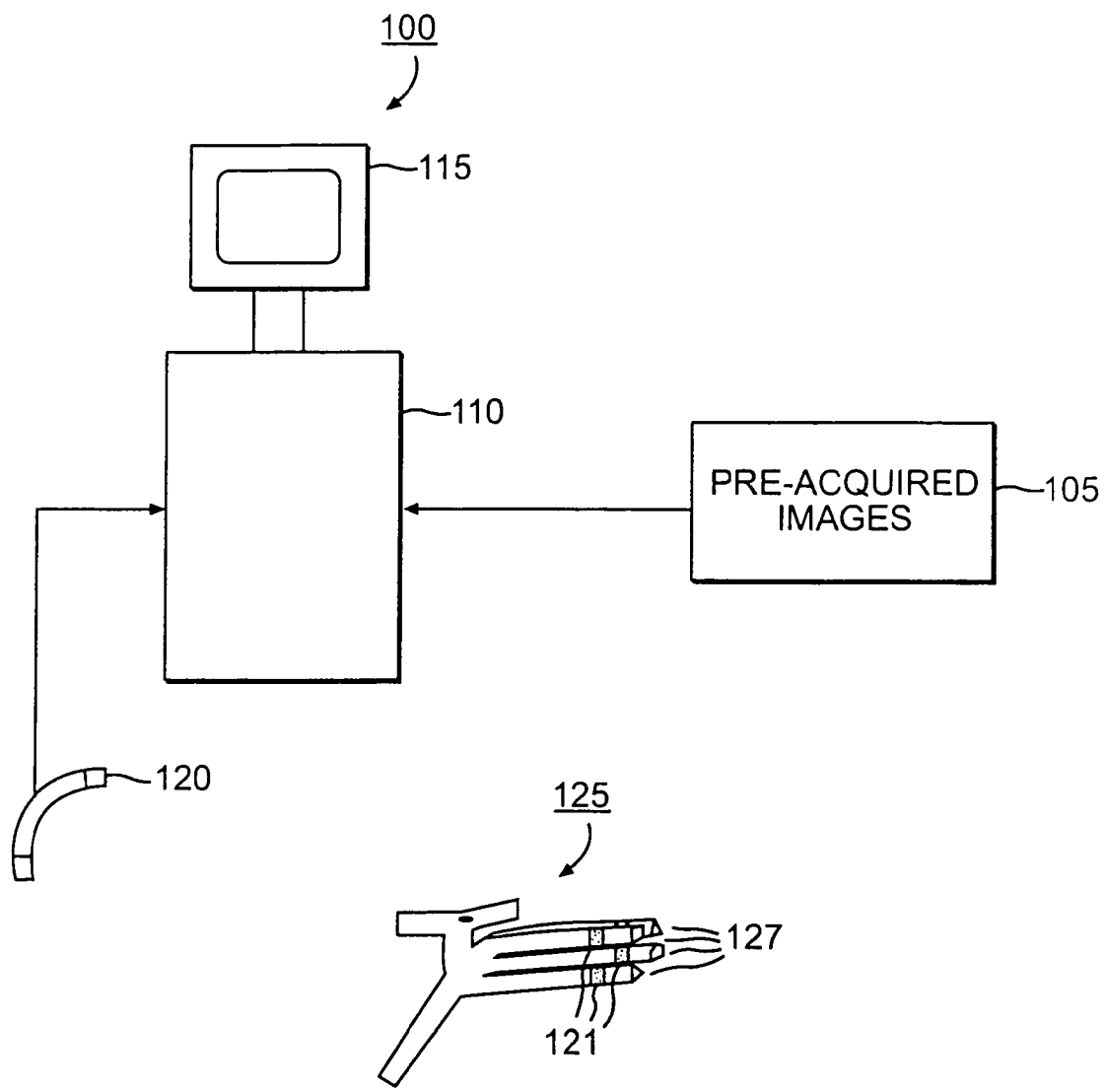
FIG. 1 is a simplified block diagram of a system for the combined positioning of multiple surgical implements consistent with the present invention.

With reference to FIG. 1, there is shown schematically an apparatus in accordance with the present invention for the combined positioning of multiple surgical implements. Image-based surgical navigation system 100 enables a surgeon to generate and display on monitor 115 a plurality of positions representing each cannula 127 of tool guide 125. Data representing one or more pre-acquired images 105 is fed to navigation computer 110. The pre-acquired images, generated prior to implement placement, typically are taken from different orientations and represent the region of interest of a patient's body which is to receive the implements. Navigation computer 110 tracks the position of tool guide 125 in real time utilizing a detector. The detector may be an sensor array 120 physically uncoupled from tool guide 125. Alternatively, the detector could also be at least one trackable marker 121 physically attached to or integrated into tool guide 125. Computer 110 then registers and displays the position of each cannula 127 with images 105 in real time to allow the surgeon to properly position and orient the tool guide into the anatomy for implement placement. The pre-acquired images 105 are superimposed on the icons representing each cannula 127 on monitor 115. While the present invention described in more detail below is exemplified by a fluoroscopic-based system used for femoral neck fracture fixation, it is not limited to the described embodiment.

Figure 2:
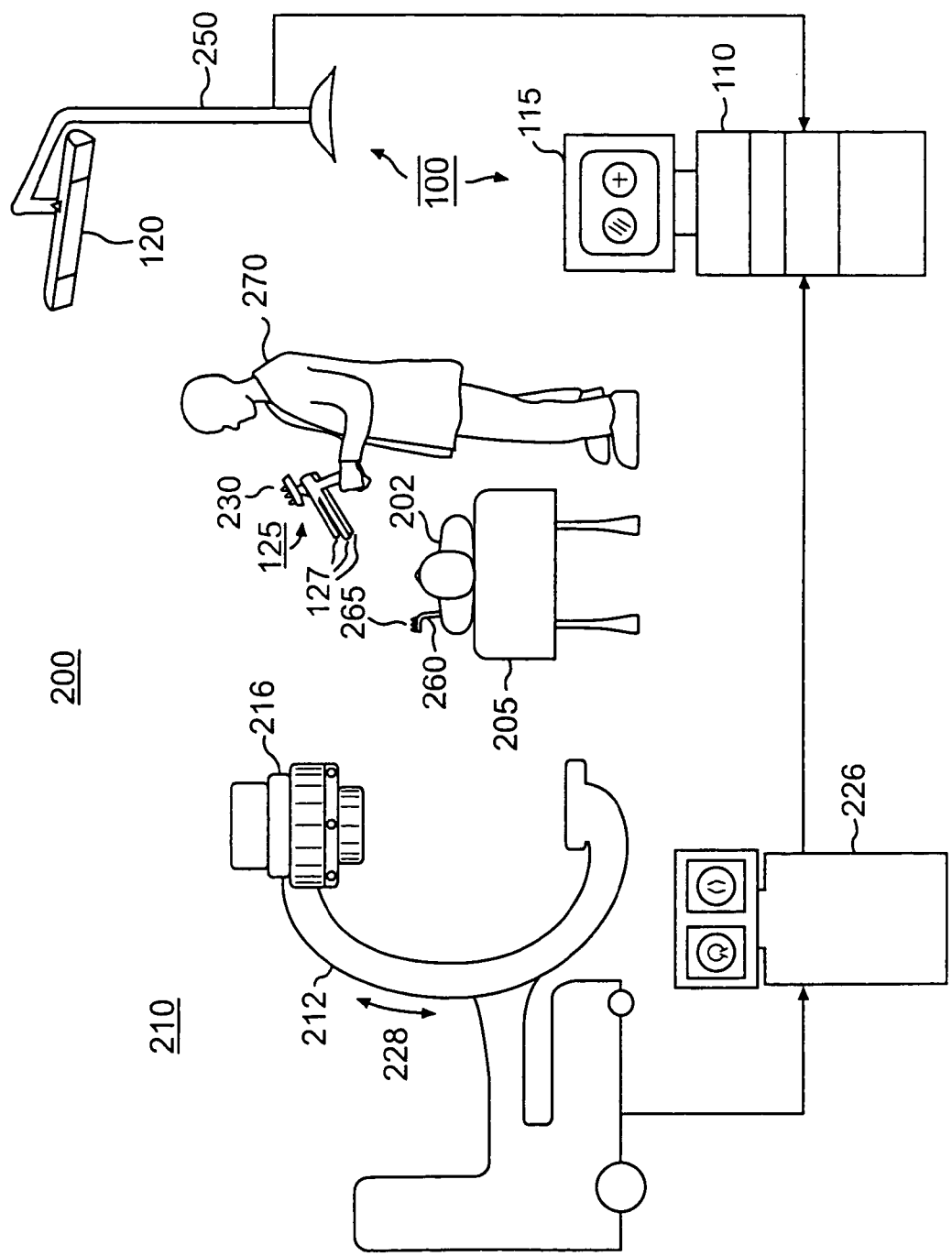
FIG. 2 is a simplified side view of an embodiment of a system for the combined positioning of multiple surgical implements consistent with the present invention.

FIG. 2 illustrates apparatus 125 in use with a preferred image-based surgical navigation system 200 according to one embodiment of the present invention. System 200, described below in sufficient detail to allow an understanding and appreciation of the present invention, is explained in greater detail in U.S. patent application Ser. No. 09/274,972 of David A. Simon et al., entitled "Navigation Guidance via Computer Assisted Fluoroscopic Imaging," filed on Mar. 23, 1999, now U.S. Pat. No. 6,470,207, issued Oct. 22, 2002, the entire disclosure of which is hereby incorporated by reference. However, it must be understood that the invention is not confined to use with this particular image guided surgical system.

Further referring to FIG. 2, an image-based surgical navigation system 200 for acquiring and displaying x-ray images appropriate for a given surgical implement procedure is shown. Pre-acquired images of patient 202 are collected when a patient, lying on platform 205, is placed within C-arm 212 of imaging device 210. The term "pre-acquired," as used herein, does not imply any specified time sequence. Pre-acquired images could be generated pre-procedurally or intra-procedurally. Preferably, the images are taken before implement positioning is performed.

C-arm 212 may be capable of rotating relative to patient 202, allowing images of the patient to be taken from multiple directions. For example, the surgeon may rotate C-arm 212 about its mechanical axis as shown by arrows 228. Usually, images are taken from two substantially orthogonal directions, such as anterior-posterior (A-P) and lateral, of the anatomy which is to receive the surgical implements. One implementation of imaging device 210 is the Model 9600 C-arm fluoroscope from OEC Medical Systems, Inc. of Salt Lake City, Utah.

It is to be understood, however, that the invention is not confined to the use of a C-arm fluoroscopic device. Other embodiments of the invention could include imaging systems which produce 3-D volumetric data. Examples of such 3-D imaging systems include computer tomography, ultrasound, or magnetic resonance imaging. Functional imaging systems such as, for example, functional magnetic resonance imaging, positron emission tomography, single photon emission tomography, or magnetoencephalography, could also be used.

Fluoroscopic images taken by imaging system 210 are transmitted to computer 226 where they may be forwarded to surgical navigation computer 110. Image transfer may be performed over a standard video connection or a digital link. Computer 110 provides the ability to display, via monitor 115, as well as save, digitally manipulate, or print a hard copy of the received images. Images, instead of, or in addition to, being displayed on monitor 115, may also be displayed to the surgeon through a heads-up display or some other type of appropriate display device.

Although computers 226 and 110 are shown as two separate computers, they alternatively could be variously implemented as a single-chassis multi-processor computer or as a single computer that performs the functions performed by individual computers 110 and 226. In the single computer case, such computer would directly receive image data from image device 210 directly and detector 120.

Further referring to FIG. 2, image-based surgical navigation system 100 generally performs the real-time tracking of tool guide 125, and, in the shown embodiment, also tracks the position of C-arm receiver section 216 and anatomical reference frame 260. This embodiment utilizes a detector which includes a sensor array 120 which is suspended by mount 250. Sensor array 120 may be located in such a manner as to provide a clear line of sight to the tracking markers on each tracked object (such as tracking markers 265, described more fully below). Sensor array 120 is coupled to computer 110 which may be programmed with software modules that analyze the signals transmitted by sensor array 120 to determine the position of each object in detector space. The manner in which the sensor array localizes the object is known in the art. See also, for example, PCT Application No. PCT/US95/12894 (Publication No. WO 96/11624) to Bucholz, the entire disclosure of which is incorporated by reference.

The tracking markers for each tracked object may be, for example, reflective markers and/or light emitting diodes (LEDs). Other devices known in the art may be used that are capable of being tracked by a corresponding detector within the scope of the invention. For purposes of illustration, and not by limitation, the tracking means may be acoustic, magnetic, optical, electromagnetic, inertial, and radiological devices known in the art. It should also be understood that different tracking markers for each tracked object can be used.

Not all of the tracking devices listed above are used in conjunction with sensor array 120. For example, a single electromagnetic tracking marker is actually a sensor which may be used to provide at least three degrees of spatial information in detector space. Some electromagnetic sensors can also provide additional attitude information, thus providing up to six degrees of positional information. Such sensors may also have no line of sight constraint which provides the advantage of functioning while embedded within a patient. The manner in which electromagnetic sensors localize an object is well known in the art. See also, for example, PCT Application No. PCT/GB93/01736 (Publication No. WO 94/04938) to Bladen, the entire disclosure of which is incorporated by reference.

In the embodiment of FIG. 2, anatomical reference frame 260, which incorporates a plurality of tracking markers 265, is attached to patient 202 during an implement procedure. The reference frame may be securely attached to the anatomy in the region of the body which is to receive the implements. Reference frame 260 may be placed in a position so that the markers are visible to sensor array 120 during the image acquisition process and the implement procedure. By sensing attached tracking markers 265, computer 110 can determine the position of the anatomy in detector space. This information is later used by computer 110 to register pixels found in the images to the position of the patient's anatomy as described in detector space. For purposes of this document, detector space is defined herein as the three-dimensional reference coordinate system associated with the detector.

Further referring to FIG. 2, multiple cannula tool guide 125 may be tracked by surgical navigation system 100 using attached tracking markers 230 in order for its position to be determined in detector space. Computer 110 integrates this information with the pre-acquired images of patient 202 to produce a display which assists surgeon 270 when performing multiple implement procedures. Representations of multiple cannulas 127 are overlaid on the pre-acquired images of patient 202 and displayed on monitor 115. In this manner, surgeon 270 is able to see the location of the cannulas relative to the patient's anatomy, and can position and orient multiple implements into the desired portion of patient's body.

Image-based surgical navigation system 100 utilized in the embodiment of the invention shown in FIG. 2 may be the same as that used in the FluoroNay™ system, which utilizes the StealthStation®. Treatment Guidance Platform, both of which are available from Medtronic Sofamor Danek, Inc.

Figure 3:
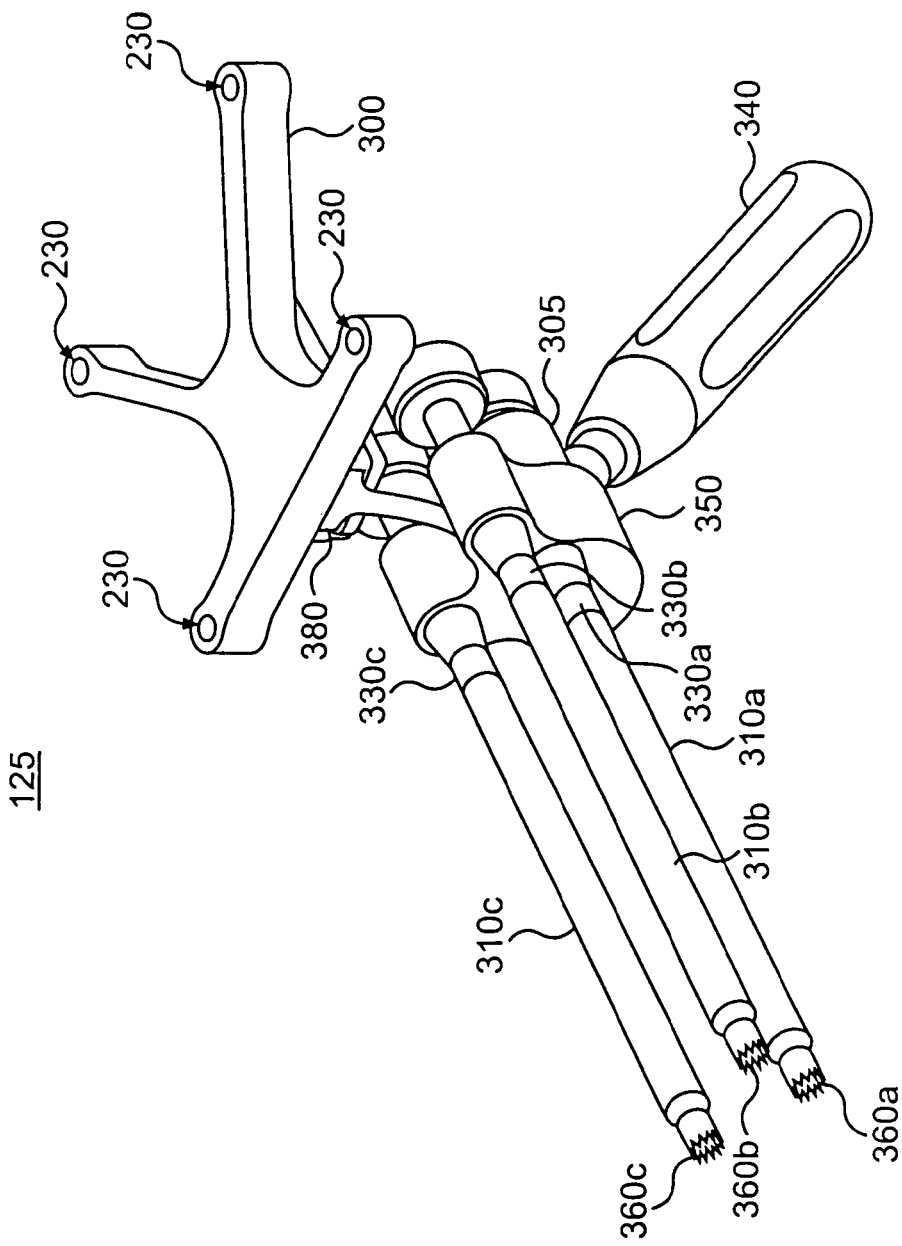
FIG. 3 is a perspective view of an embodiment of a tool guide consistent with the present invention.

FIG. 3 is a perspective drawing of an embodiment of tool guide 125 which is optimized for the combined positioning of cannulated screws to secure femoral neck fractures. A plurality of tracking markers 230 are positioned at points on the upper surface of frame 300. Frame 300 firmly attaches to a body 305 of tool guide 125 by sliding onto a dovetail formed on the top of mounting post 380. Frame 300 may be interchanged with other frames which utilize different sizes or shapes, or tracking markers of a different type. In the embodiment shown in FIG. 3, tracking markers 230 may be infrared LEDs and/or reflective markers such as those supplied by Northern Digital Inc.

For the embodiment shown in FIG. 3, tool guide 125 includes three substantially parallel cannulas 310a, 310b, 310c. Cannula 310a has a fixed length and the other cannulas 310b, 310c have lengths which are variable. However, in general, the invention could comprise a tool guide where all the cannulas, or any subset thereof, may have variable lengths. The variable length cannulas can be independently adjusted by the use of threaded means 330, which screw into interchangeable fixture 350 and are locked in place using a set screw or jam nut (not shown). Variable length cannulas allow tool guide 125 to adapt to the varying surface shapes associated with different bone structures. The surgeon, using information from the pre-acquired images, can make the proper length adjustment to each adjustable cannula during the pre-operative planning stage of the medical procedure. The cannulas may possess teeth 360a, 360b, 360c at their distal end in order to effectively grip the patient's bone.

Furthermore, tool guide 125 may have cannulas which have inner and outer diameters that are also variable. These diameters may be altered by simply interchanging a given cannula with another having differing diameters, or alternatively, using cylindrical adapters to modify the diameters of an existing cannula. For example, the inner diameter of the lumen may be reduced by inserting a reduction sleeve which extends the length of the cannula. Various reductions in lumen diameter can be achieved through the insertion of one or more reduction sleeves. Alternatively, the outer diameter of a cannula may be increased in a similar manner by sliding one or more expansion sleeves over the outside of the cannula. Other embodiments of tool guides can be provided by changing fixture 350. For example, one such interchangeable fixture 350 could have cannulas with non-parallel, fixed angular offsets. In the embodiment of FIG. 3, cannulas 310b and 310c can be removed by unscrewing them from fixture 350. The fixture may then be slid off cannula 310a and replaced with another having different characteristics. For example, the number of cannulas can be varied by utilizing fixtures which have a different number of attachment points. Additionally, the relative geometry, or spread, between the cannulas can be varied by utilizing fixtures which have attachment points in different relative locations. Finally, the relative angulations among the cannulas may be altered from a parallel configuration by employing a fixture having attachment points with fixed angular offsets.

Many different types of cannulas could be used with the invention in its broadest aspects. In the embodiment shown in FIG. 3, the cannulas 310a, 310b, 310c are preferably substantially rigid tubular members each having a lumen extending therethrough that is configured to allow for passage of surgical implements, such as drills or other tools, and/or devices, such as cannulated screws, nails, etc.

The surgeon typically holds and manipulates tool guide 125 by grasping handle 340 shown in FIG. 3. Alternatively, the invention could also be physically manipulated by a machine, such as, for example, a robotic arm. Machine manipulation could be facilitated through a coupling on body 305 which could allow tool guide 125 to be removably attached to a mechanized placement system. This arrangement could facilitate highly accurate placement of surgical implements, without usage of handle 340.

Figure 4:
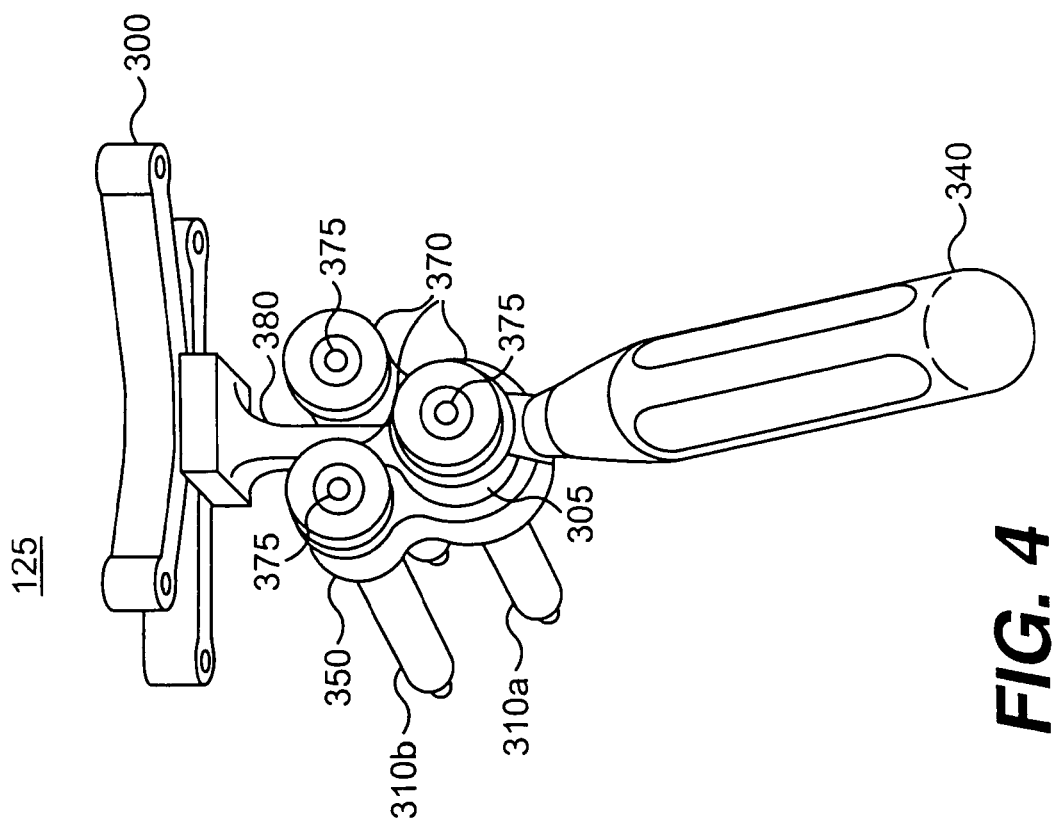
FIG. 4 is a rear view of the embodiment of the tool guide shown in FIG. 2.

FIG. 4 is a rear-view perspective drawing of the embodiment of tool guide 125 shown in FIG. 3. Situated towards the proximal end of the each cannula is a flange 370, attached to body 305. At the flange center is a countersunk hole 375 which leads to the lumen of the cannula. Flange 370 and hole 375 is a surgical implement receiver which assists the surgeon in the placement of implements down the cannulas once tool guide 125 is properly positioned in the patient's body. For a procedure, for example, to secure a femoral neck fracture, a drill with an attached guide wire is sequentially placed down each cannula after tool guide 125 has been appropriately positioned relative to the patient's body. The surgeon drills into the bone in order to anchor the guide wire. A cannulated screw is then placed over each guide wire and the screw is tapped into the bone at the fracture site. Once the screws are in place and secured, the guide wires are removed along with tool guide 125.

Figure 4A:
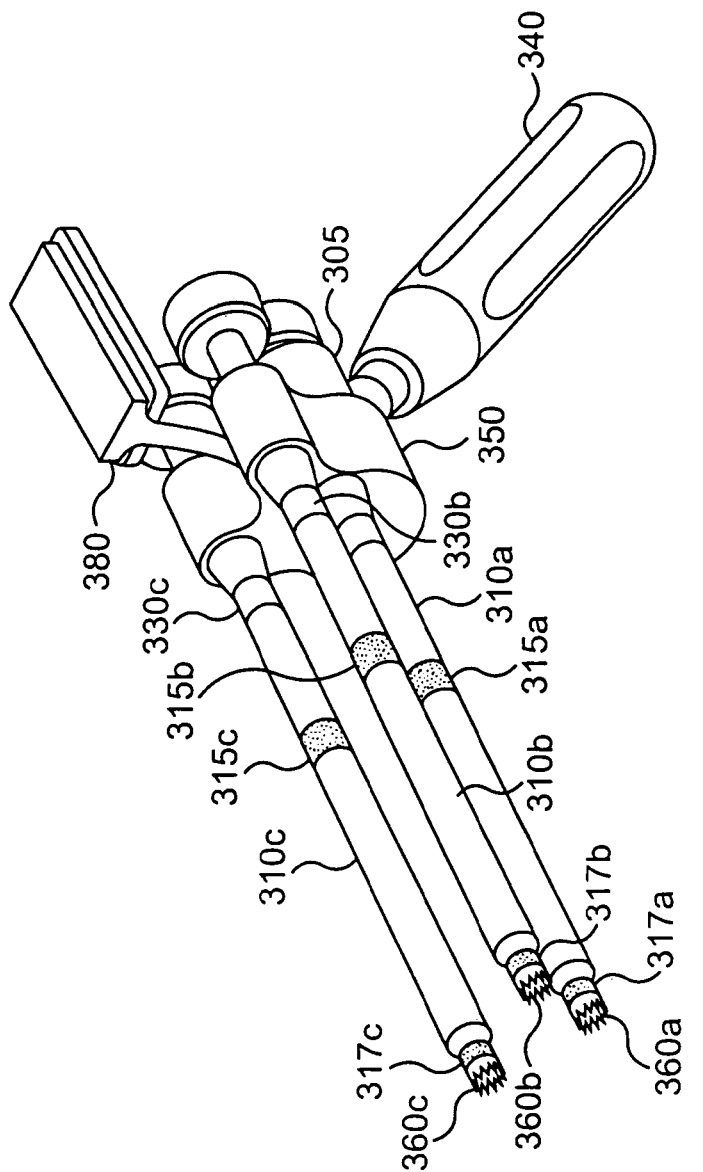
FIG. 4a is a perspective view of another embodiment of a tool guide consistent with the present invention.

FIG. 4a shows an embodiment of a tool guide having electromagnetic sensors attached to cannulas 310a, 310b, and 310c. Electromagnetic sensors may be placed at the approximate mid-point of each cannula, as shown by 315a, 315b, and 315c, and/or they may be placed towards the tips of each cannula as shown by 317a, 317b, and 317c. Electromagnetic sensor groups 315a-c and 317a-c may be used separately or in conjunction with each other. Utilizing both groups can allow for the extraction of trajectory information of each cannula. Typically, each cannula would be equipped with separate electromagnetic sensors, however; some embodiments may have just one, or any subset of the total number of cannulas, equipped with electromagnetic sensors.

Figure 4B:
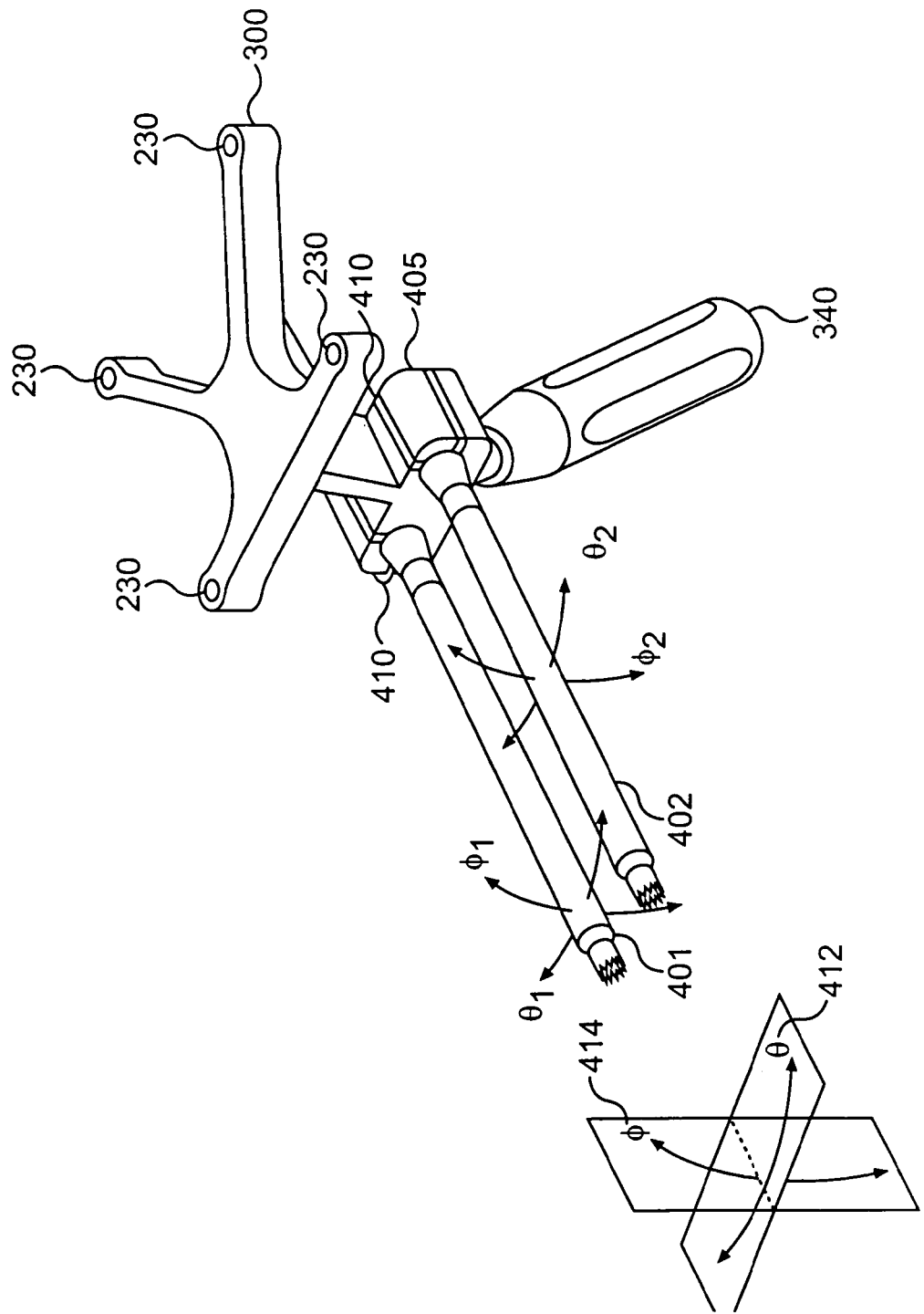
FIG. 4b is another embodiment of the tool guide having the ability to adjust the relative angles between the cannulas.

FIG. 4b exemplifies another embodiment of a tool guide having cannulas with adjustable relative angles. Cannulas 401 and 402 are set in fixture 405 such that the base of each cannula can pivot within the fixture. The angle of each cannula can be varied independently in the azimuth, .theta. ($\theta$), 412 and elevation, .phi. ($\phi$), 414 directions relative to fixture 405. For example, the cannula 401 can be adjusted for azimuth $\theta_1$ and elevation $\phi_1$ and the cannula 402 can be adjusted for azimuth $\theta_2$ and elevation $\phi_2$ independently of one another. After the angles for each cannula have been adjusted as desired, mechanism 410 can lock each cannula in place. Mechanism 410 can be a friction or compression lock, or any other type of locking mechanism known in the art. The orientation of cannulas 401, 402 shown as mutually parallel in FIG. 4b is only for purposes of explanation, and not limitation. Other embodiments which allow the cannulas to have a varying angular position which are known in the art could be used. It should also be understood that the tool guide shown in FIG. 4b could have any number of cannulas, and in addition to each angle being variable, each cannula could be individually adjusted in length.

Figure 5:
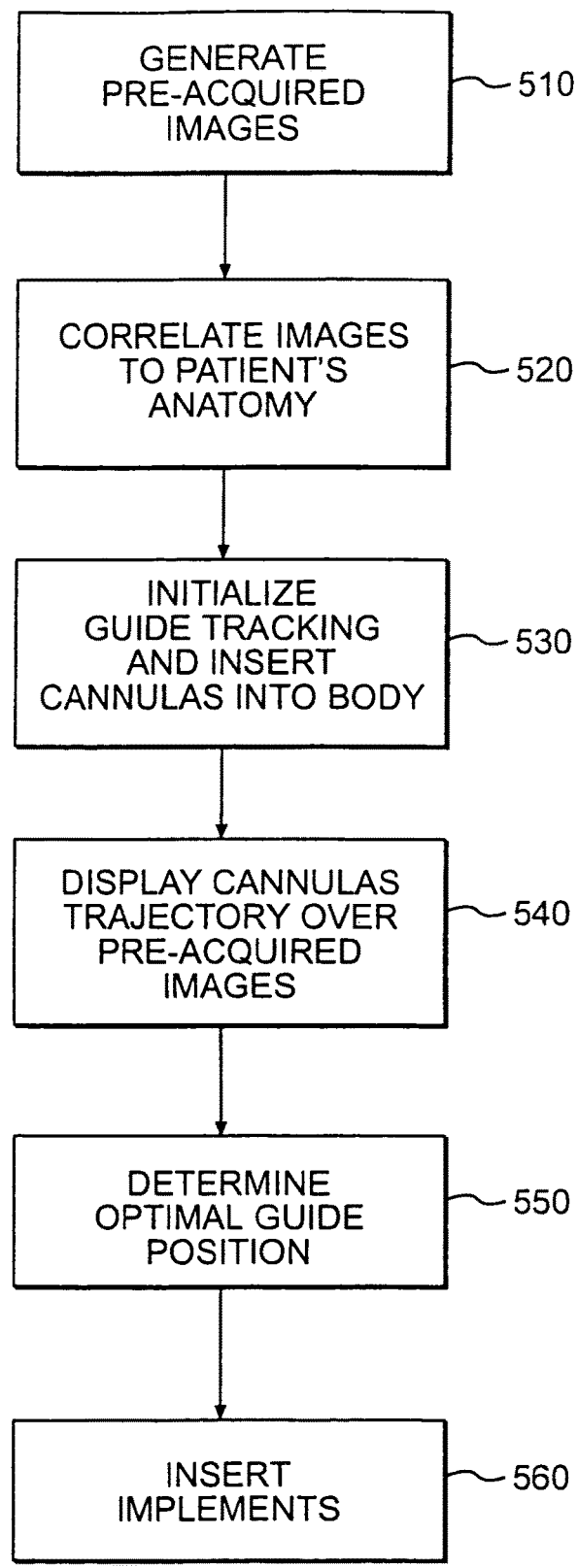
FIG. 5 is a block diagram of a process used to place surgical implements consistent with the present invention.

FIG. 5 is a flowchart illustrating methods for multiple implement positioning using image-based surgical navigation techniques. The surgeon may begin by acquiring one or more images of a patient. In one embodiment, these may be acquired with fluoroscopic x-ray imager 210, as shown in system of FIG. 2. Alternatively, such images may be acquired with an imaging device with provides 3-D volumetric data (step 510).

Computer 110 then retrieves a pre-acquired image and correlates the spatial coordinates defined by the images, known as image space, with the spatial coordinates defined by the detector, known as detector space. As shown in the embodiment of FIG. 2, computer 110 may retrieve a pre-acquired image from C-arm control computer 226. Computer 110 then determines location information of receiver section 216, and anatomical reference frame markers 265, using sensor array 120. Computer 110 then correlates the images to anatomical reference marker 260, by determining and applying a geometric transform well known to those skilled in the art. Computer 110 then stores the image along with its positional information (step 520). The processes described in step 520 are repeated for each image to be acquired.

The implement placement procedure starts once a detector and computer 110 detect and track the position of tool guide 125 relative to patient 202 in detector space. With this information, computer 110 dynamically calculates, in real time, the projections of cannulas 127 into each image as tool guide 125 is moved by surgeon 270. Typically, the surgeon places the cannulas into the patient percutaneously into the region of interest to position the implements (step 530). However, the invention can be used with other surgical techniques.

Graphical representations of cannulas are superimposed on pre-acquired images and displayed on monitor 115. The cannulas can be displayed, simultaneously if desired, and in real time relative to the patient's anatomy (step 540). The surgeon, utilizing the display, can then manipulate tool guide 125 and position cannulas 127 in the region of interest. Using real-time display 115, the physician gets feedback on how the cannulas are oriented relative to the anatomy and then determines the optimal orientation (step 550). Once this is determined, the surgeon will then sequentially place the implements into the patient. If, for example, the procedure involves the fixation of a femoral neck fracture as previously described, the surgeon first places a drill with an attached guide wire down the cannula to drill into the bone at the fracture site and then anchor the guide wire into the bone.

The surgeon then places a cannulated screw over the guide wire and down into the cannula. The screw taps into the bone at the fracture site and pulls the separate pieces of bone together. This process is repeated for each cannulated screw while the surgeon steadily holds tool guide 125 in place. Alternatively, the surgeon may place the guide wires using the cannulas and then remove the guide from patient's body. The surgeon would then position the screws by placing them over each guide wire, leading them to the bone into the fracture site (step 560).

Figure 6:
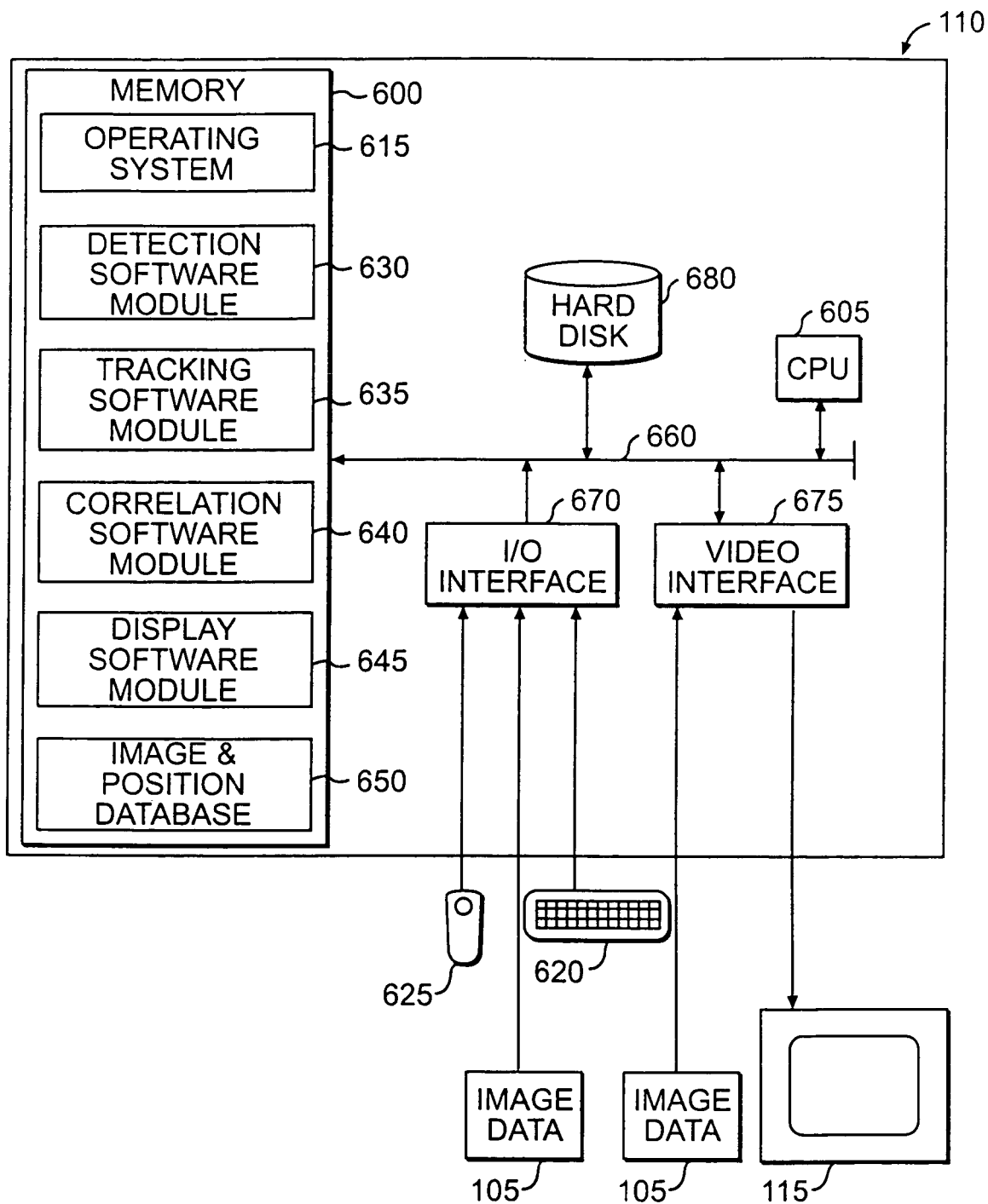
FIG. 6 is a simplified block diagram of an exemplary computer system used in the surgical navigation system in accordance with one embodiment of the invention.

Referring to FIG. 6, components and modules of a computer system 110 used to perform various processes of the present invention are described. Although a STEALTH STATION® image guided system manufactured by Medtronic Sofamor Danek has been identified, it will be appreciated that the present invention may be utilized with other types of computer systems. One aspect of the computer system 110 includes a graphical user interface system operating in conjunction with a display screen of a display monitor 115. The graphical user interface system is preferably implemented in conjunction with operating system 615 running computer 110 for displaying and managing the display objects of the system. The graphical user interface is implemented as part of the computer system 110 to receive input data and commands from a conventional keyboard 620 and mouse 625. For simplicity of the drawings and explanation, many components of a conventional computer system have not been illustrated such as address buffers, memory buffers, and other standard control circuits because these elements are well known in the art and a detailed description thereof is not necessary for understanding the present invention. A computer program used to implement the various steps of the present invention is generally located in memory unit 600, and the processes of the present invention are carried out through the use of a central processing unit (CPU) 605. Those skilled in the art will appreciate that the memory unit 600 is representative of both read-only memory and random access memory. The memory unit also includes a database 650 that stores data, for example, image data and tables, including such information as position data and geometric transform parameters, used in conjunction with the present invention. CPU 605, in combination with the computer software comprising operating system 615, detection software module 630, tracking software module 635, calibration software module 640, and display software module 645, controls the operations and processes of computer system 110. The processes implemented by CPU 605 may be communicated as electrical signals along bus 660 to an I/O interface 670 and a video interface 675.

Detection software module 630 utilizes signals from the detector and performs the processes associated with creating a coordinate reference system and detecting positions of reference images for use in connection with the present invention and are known to those skilled in the art. Tracking software module 635 performs the processes necessary for tracking objects in an image guided system as described herein and are known to those skilled in the art. Correlation software module 640 computes the geometric transform which registers the images to the detector space, and thus the patient's anatomy.

Display software module 645 applies, and if necessary, computes the offsets between tool guide tracking markers 230 and the cannulas in order generate an icon representing each cannula for superposition over the images. For tool guides with fixed cannulas, these offsets can be measured once and stored in database 650. The user would then select from a list of tool guides which one was being used in the procedure so the proper offsets are applied by display software module 645. For tool guides with variable lengths and angulations, the offsets could be measured manually and entered via keyboard 620, or measured using the navigation system 100 in conjunction a tracked pointer or tracked registration jig (not shown). If a tracked pointer is used, the user will touch the tip and tail of each cannula while the tool guide is being tracked. The offsets are computed by display software module 645 and stored for later use. Similarly, if a tracked registration jig is used, the tool guide is placed within the jig while it is being tracked. The jig will measure the positions of the cannulas and display software module 645 will again compute the offsets and store them for later use in database 650.

Pre-acquired image data 105 can be fed directly into computer 110 digitally through I/O interface 670, or may be supplied as video data through video interface 675. In addition, items shown as stored in memory can also be stored, at least partially, on hard disk 680 if memory resources are limited. Furthermore, while not explicitly shown, image data may also be supplied over a network, through a mass storage device such as a hard drive, optical disks, tape drives, or any other type of data transfer and storage devices which are known in the art.

Figure 7:
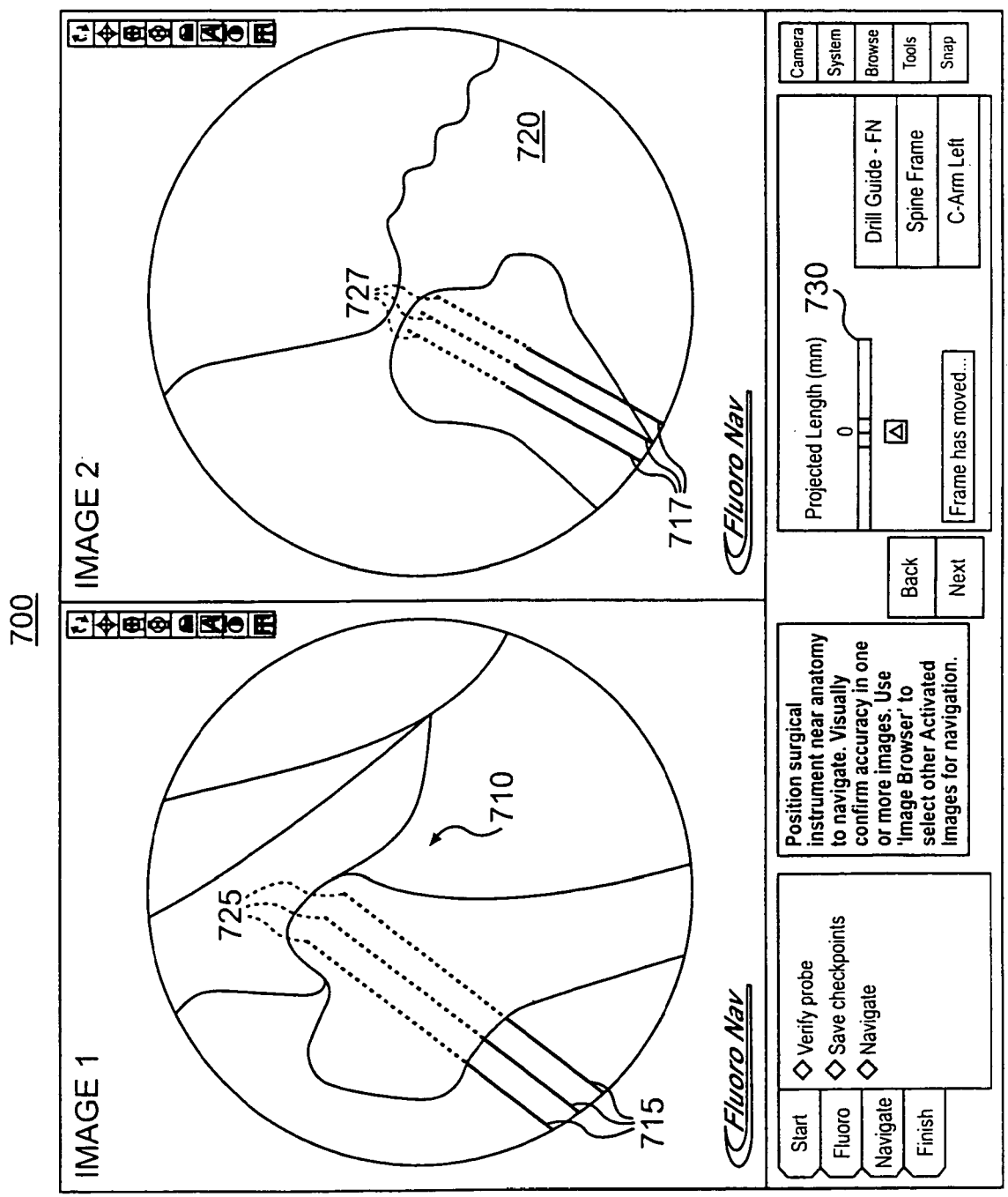
FIG. 7 is an exemplary diagram of a display consistent with an embodiment of the invention showing the trajectory of cannulas superimposed on images of a patient's anatomy.

FIG. 7 shows an exemplary diagram of display 700 illustrating an iconic graphical overlay of the cannulas for the preferred embodiment. Display 700 is presented to the surgeon on monitor 115 of computer system 110. The left side of FIG. 7 shows a fluoroscopic image of an anterior-posterior view of a hip and femoral neck bone 710. Graphical overlays 715 are the iconic superposition of all the cannulas 127 attached to tool guide 125 within image 710. Graphical overlays 715 are directional indicators, displaying the position and orientation of each cannula. In the embodiment shown in FIG. 7, these directional indicators are shown as lines, but other symbols may be used. As the surgeon moves tool guide 125, computer 110 recalculates and displays the new locations of the graphical overlays 715. The surgeon can use image 710 and overlays 715 to visualize, in real-time, the position and orientation of the cannulas relative to the patient's anatomy.

For the embodiment shown in FIG. 2, the surgeon would like to acquire two substantially orthogonal fluoroscopic images of patient 202, such as images from an anterior-posterior view and a lateral view of the anatomy of interest. These two complementary views help the surgeon to better visualize how the cannulas are situated in the patient's anatomy. The orthogonal views are related to one another by a 90 degree rotation about the major axis of the patient (the axis running along the length of the patients body). The fluoroscopic image taken from the lateral view 720 is shown on the right side of FIG. 7, along with graphical overlays 717 showing the locations of the cannulas 127.

In certain situations, the surgeon may wish to know where the tip of the cannulas would be if cannulas were projected along a line give by a tool guide's current trajectory. At the surgeon's command, computer 110 may calculate and display this projection based upon the current orientation and position of the cannulas. This orientation and position are determined by tracking the tip and the tail of each cannula. The estimated position of the tip can be calculated by computer 110 through projecting a fixed distance beyond the cannulas' tips in the direction of the line formed by each cannula's tip and tail. The estimated position, or "look-ahead" trajectory, would be represented by a graphical overlay. As shown in FIG. 7, exemplary "look-ahead" trajectories 725 and 727 are shown in a different line styles from overlay 715 and 717, respectively. This difference could also be a change in color, type, or texture between the look-ahead trajectory 725, 727 and the current position 715, 717. Computer 110 may vary the length of the look-ahead trajectory 725, 727 as directed by the surgeon through the graphical user interface control 730 and computer keyboard 620 or mouse 625. In this manner, computer 110 assists the surgeon in visualizing where the cannulas would be in the patient if they were advanced a predetermined distance into the body of the patient.

Although the look-ahead technique described above projected the graphical representation of the cannulas into the image, there is no requirement that the cannulas' graphical representation be in the space of the image for look ahead trajectory 725, 727 to be projected into the image. In other words, for example, the surgeon may be holding tool guide 125 above the patient and outside the space of the image, so that the representation of the cannulas does not appear in the images. However, it may still be desirable to project ahead portion 725, 727 into the image to facilitate planning of the implement procedure.

The look-ahead technique could be extended to include virtual implants. Graphical overlays representing implant structures such as prosthetic devices, plates, and fasteners such as screws, nails, etc., could be shown on display 115 during and after their placement into the patient's body. These graphical overlays would provide additional information regarding the implants without involving the generation of new images.

When cannulas 127 are perpendicular to the plane of the fluoroscopic image, the graphical overlay of the cannulas may virtually collapse to a point, potentially making it difficult to view them. To alleviate this, computer 110 may optionally use a different graphical representation of cannulas 172 when the distance in the image plane between the tip and tail of the cannulas 127 becomes smaller than some fixed distance.

The foregoing description is presented for purposes of illustration and explanation. It is not intended to be exhaustive or to limit the invention to the precise form disclosed, and modifications of variations are possible in light of the above teachings or may be acquired from practice of the invention. The principles of the invention and its practical application enable one skilled in the art to utilize the invention in various embodiments and with various modifications as are suited to the particular use contemplated.

For example, pre-acquired images obtained from modalities different than the C-arm fluoroscope x-ray imager may be used with the invention. Such modalities could supply 3-D volumetric data and may also include functional information. Such modalities may include, by way of example only, computer tomography, ultrasound, or magnetic resonance imaging. Imaging modalities which may provide functional information include functional magnetic resonance imaging, positron emission tomography, single photon emission tomography, magnetoencephalography, or any other modality known to those skilled in the art.

Furthermore, the invention is not limited to the fixture of femoral neck fractures, but can be used for many different types of procedures such as the distal locking of intramedullary nails, in placing implements such as interbody fusion devices into the spine, anterior cervical plating systems, etc., or any other application where two or more implements are to be placed, especially multiple implements having fixed relative positions and angulations.

What is claimed is:

1. An apparatus for the placement of surgical implements, comprising:
   a plurality of cannulas;
   a fixture coupled to the plurality of cannulas, (a) wherein the fixture includes a body member having a plurality of attachment locations such that each cannula of the plurality of cannulas is attached at one attachment location of the plurality of attachment locations, wherein each one attachment location is spaced apart and fixed relative to each other one attachment location, (b) a first cannula of the plurality of cannulas is further individually adjustable via the body member at a first attachment location of the plurality of attachment locations to (i) vary and select at least an angular position of the first cannula relative to the body member of the fixture and (ii) is adjustable to vary a length and select the length of the first cannula relative to the body member of the fixture, and (c) a post extending from the fixture; and
   a frame having at least one point, wherein at least one trackable marker is connected to the frame at the at least one point, wherein the frame is selectively and removably interchangeably connected to the fixture via the post at a location spaced apart from the plurality of attachment locations and the plurality of cannulas;
   wherein the at least one trackable marker is configured to be connected and fixed to the fixture by the frame and tracked with a detector in a detector space to determine a three-dimensional location of the plurality of cannulas in the detector space when the at least one trackable marker is selectively connected and fixed to the fixture;
   wherein the determined location of the plurality of cannulas is determined relative to a patient based at least on the tracked at least one trackable marker; and
   wherein a graphical representation is operable to be displayed with a monitor, wherein the graphical representation simultaneously displays all of the plurality of cannulas at the determined three-dimensional location of the plurality of cannulas, wherein the graphical representation is operable to be superimposed on a pre-acquired image at the determined three-dimensional location of the plurality of cannulas including at least a tip of each cannula of the plurality of cannulas.

2. The apparatus of claim 1, further comprising: a locking mechanism having a moveable portion to lock at least one of the selected length or the selected angular position of the first cannula relative to the fixture at the t attachment location of the plurality of attachment locations.

3. The apparatus of claim 2, wherein each cannula of the plurality of cannulas is configured to vary at least one of its length relative to the fixture or vary its angular position relative to the fixture.

4. The apparatus of claim 3, wherein the locking mechanism is configured to lock each cannula of the plurality of cannulas in respective at least one selected length or selected angular position relative to the fixture.

5. The apparatus of claim 4, wherein at least two cannulas of the plurality of cannulas are not parallel when locked with the locking mechanism.

6. The apparatus of claim 2, further comprising:
   a handle member extending from the fixture configured to be supported by a hand of a user;
   wherein the handle member is configured to allow the user to move all of the plurality of cannulas, the fixture while coupled to the plurality of cannulas, and the frame while connected to the fixture;

wherein the locking mechanism includes a threaded connection of the first cannula to the fixture.

7. The apparatus of claim 2, further comprising:
wherein the graphical representation simultaneously represents all of the plurality of cannulas and includes a first portion that includes a tip of each cannula of the plurality of cannulas and a look-ahead trajectory from the tip of each cannula of the plurality of cannulas.

8. The apparatus of claim 7, further comprising:
the monitor configured to simultaneously display the pre-acquired image and the graphical representation of all of the plurality of the cannulas.

9. An apparatus for the placement of surgical implements, comprising:
a plurality of cannulas;
a fixture having a body coupled to the plurality of cannulas, wherein the body of the fixture has a passage that is configured to accommodate at least one cannula of the plurality of cannulas being individually adjustable to vary and select a length and vary and select an angular position of the at least one cannula relative to the fixture, wherein the angular position is variable in at least one of azimuth in a horizontal reference plane relative to the fixture or elevation in a vertical reference plane relative to the fixture;
a plurality of interchangeable frames, each frame of the plurality of interchangeable frames slidably connected to the body of the fixture via a post at a location separate and spaced apart from the passage and the plurality of cannulas, wherein each frame of the plurality of interchangeable frames slidably connects to the fixture with a dovetail connection; and
at least one trackable marker on each frame of the plurality of interchangeable frames associated with the plurality of cannulas by slidable connection of respective one frame of the plurality of interchangeable frames to the fixture at the location separate and spaced apart from the plurality of cannulas;
wherein the at least one trackable marker separate from the passage and the plurality of cannulas is configured to be tracked to determine a location of the plurality of cannulas with a detector.

10. The apparatus of claim 9,
wherein at least a first frame and a second frame of the plurality of interchangeable frames each have a different type of trackable marker;
wherein each frame of the plurality of interchangeable frames is separately, individually, and selectively connectable to the fixture via the dovetail connection.

11. The apparatus of claim 10, wherein the at least one cannula of the plurality of cannulas is individually adjustable to vary at least one of its inner diameter or outer diameter with one or more selected sleeves.

12. The apparatus of claim 10, further comprising:
a locking mechanism having a locking member that is moveable to lock at least one of the selected length or the selected angular position of the at least one cannula relative to the fixture;
wherein at least a location of a tip of the at least one cannula is operable to be determined relative to the fixture;
wherein the fixture includes a first fixture and a second fixture, wherein the first fixture is configured to be removably connected to the plurality of cannulas and the second fixture connected to at least a sub-plurality of the plurality of cannulas.

13. The apparatus of claim 12, further comprising:
an instrument location system; and
a monitor configured to display a pre-acquired image;
wherein the at least one trackable marker is configured to be detected by the instrument location system to determine a position of the plurality of cannulas in a detector space;
wherein a graphical representation of all of the plurality of cannulas simultaneously is operable to be superimposed on the pre-acquired image at the determined position of the plurality of cannulas;
wherein the graphical representation superimposed on the pre-acquired image are displayed with the monitor.

14. The apparatus of claim 13, wherein the instrument location system is configured to determine at least the location of the tip of the at least one cannula as the graphical representation and at least one look-ahead trajectory.

15. An apparatus for the placement of a surgical implement, comprising:
a fixture having a body having a plurality of passages;
a plurality of cannulas coupled to the body of the fixture, wherein the plurality of cannulas extend through the plurality of passages and from the body of the fixture;
a post mounted to the body of the fixture away from the plurality of passages, wherein the post extends from the body of the fixture; and
a frame selectively and interchangeably connected to the post extending from the body of the fixture, wherein the frame has at least one trackable marker and the frame is removably and fixably interconnected to the fixture via the post, but separate from the plurality of passages and the plurality of cannulas while being associated with the plurality of cannulas to determine a location of the plurality of cannulas;
wherein the at least one trackable marker is configured to be detected by an instrument location system to determine a three-dimensional position of the plurality of cannulas;
wherein at least one cannula of the plurality of cannulas is independently adjustable to at least one of vary a length or vary at least one angular position relative to the fixture and at least one other cannula of the plurality of cannulas;
wherein the fixture is configured with at least one passage of the plurality of passages that accommodates the at least one cannula to be individually adjustable to vary the at least one angular position relative to the body of the fixture;
wherein the length and the at least one angular position are both variable relative to the post;
wherein a position of a tip of the at least one cannula of the plurality of cannulas is determinable relative to the at least one trackable marker.

16. The apparatus of claim 15,
further comprising:
a cannula trackable marker attached to at least one cannula of the plurality of cannulas;
wherein the at least one trackable marker includes a plurality of trackable markers.

17. The apparatus of claim 15, wherein the frame includes a plurality of interchangeable frames, wherein each frame of the plurality of frames is configured to be individually removably and fixably interconnected to the fixture;
wherein each frame of the plurality of frames is separate from the plurality of cannulas.

18. The apparatus of claim 17, wherein at least two of the interchangeable frames having a different type of trackable marker.

19. The apparatus of claim 18, further comprising:
an instrument location system; and
a monitor configured to display a pre-acquired image;
wherein the at least one trackable marker is configured to be detected by the instrument location system to determine a position of the plurality of cannulas in a detector space;
wherein a graphical representation of all of the plurality of cannulas simultaneously is operable to be superimposed on the pre-acquired image at the determined position of the plurality of cannulas;
wherein the graphical representation superimposed on the pre-acquired image are displayed with the monitor.

20. The apparatus of claim 17, wherein at least one cannula of the plurality of cannulas is individually adjustable to vary at least one of its inner diameter or outer diameter.

21. The apparatus of claim 15, further comprising: a peripheral structure, coupled to the body of the fixture, configured to allow maneuvering the plurality of cannulas during a surgical procedure to place the surgical implement.

22. The apparatus of claim 21, wherein the fixture includes a plurality of fixtures, wherein each fixture of the plurality of fixtures is interchangeable relative to the peripheral structure, wherein each fixture is configured to be removably connected to the plurality of cannulas and to be removed from the plurality of cannulas, wherein at least one fixture of the plurality of fixtures may be configured to be connected to at least a sub-plurality of the plurality of cannulas, wherein each fixture is configured to accommodate at least one of: a variable number of cannulas, cannulas having a plurality of relative placements, or cannulas having a plurality of fixed relative angles.

23. The apparatus of claim 21, wherein the peripheral structure is a handle operable to be grasped by a user and to support, hold, and move the fixture by the user;
wherein the handle is configured to allow the user to move all of the plurality of cannulas, the fixture while coupled to the plurality of cannulas, and the frame while connected to the fixture.

24. The apparatus of claim 21, wherein the peripheral structure is a machine configured to manipulate the apparatus.

25. The apparatus of claim 15, wherein the at least one angular position is an azimuth angular position measured in a horizontal reference plane associated with the fixture.

26. The apparatus of claim 15, wherein the at least one angular position is an elevation angular position measured in a vertical reference plane associated with the fixture.

27. The apparatus of claim 15, wherein at least one cannula of the plurality of cannulas includes a serrated structure configured to grip portions of a patient's anatomy.

28. The apparatus of claim 15, wherein the at least one trackable marker is selected from a group comprising a reflective marker, a light emitting marker, an acoustic marker, a magnetic marker, an optical marker, an electromagnetic marker, a radiological marker, and combinations thereof.

29. An apparatus for the placement of surgical implements, comprising:
a plurality of cannulas each defined at least in part by an elongated member extending from a first proximal end to a second distal end, the elongated member defining a lumen extending from the first proximal end to the second distal end;
a fixture, (a) wherein the fixture includes a body member having a plurality of attachment locations such that each cannula of the plurality of cannulas is attached at one location of the plurality of attachment locations, and (b) a first cannula of the plurality of cannulas is further individually adjustable via the body member at a first attachment location of the plurality of attachment locations to (i) vary and select at least an angular position of the first cannula relative to the body member of the fixture and (ii) is adjustable to vary a length and select the length of the first cannula relative to the body member of the fixture;
a mounting post extending from a first end to a second end, the first end of the mounting post coupled to the fixture;
a mounting base coupled to the second end of the mounting post; and
a plurality of interchangeable frames, each frame of the plurality of interchangeable frames slidably connected to the body member of the fixture via the mounting post at a location separate and spaced part from the plurality of cannulas, wherein each frame of the plurality of interchangeable frames slidably connects to the fixture with a dovetail connection; and
at least one trackable marker on each frame of the plurality of interchangeable frames associated with the plurality of cannulas by slidable connection of a respective one frame of the plurality of interchangeable frames to the fixture at the location separate and spaced apart from the plurality of cannulas;
wherein the mounting base has the dovetail connection formed on a top surface of the mounting base.

30. The apparatus of claim 29, wherein the dovetail connection defines a pair of opposed undercut dovetail grooves formed along the top surface of the mounting base.

31. The apparatus of claim 29, wherein the dovetail connection has a first planar surface and a second planar surface, wherein the first planar surface and the second planar surface are positioned at an acute angle relative to one another.

32. The apparatus of claim 29, wherein the dovetail connection is configured to slidably receive each frame of the plurality of interchangeable frames, wherein the at least one trackable marker includes four reflective optical trackable markers positioned on each frame of the plurality of interchangeable frames.

* * * * *

UNITED STATES PATENT AND TRADEMARK OFFICE
CERTIFICATE OF CORRECTION

| | | |
|---|---|---|
| PATENT NO. | : 10,898,153 B2 | |
| APPLICATION NO. | : 13/012356 | |
| DATED | : January 26, 2021 | |
| INVENTOR(S) | : Anthony J. Melkent et al. | |

It is certified that error appears in the above-identified patent and that said Letters Patent is hereby corrected as shown below:

On the Title Page

Page 6, Column 2, item (56), Other Publications, Line 16, delete ""Three-Dimensinal" and insert --Three-Dimensional-- therefor Page 7, Column 2, item (56), Other Publications, Line 46, delete "Fluorscopic" and insert --Fluoroscopic-- therefor Page 7, Column 2, item (56), Other Publications, Line 52, delete "Comptuer" and insert --Computer-- therefor Page 8, Column 1, item (56), Other Publications, Line 27, delete "Imgaging" and insert --Imaging-- therefor In the Claims Column 12, Line 48, in Claim 2, delete "t" and insert --first-- therefor Column 13, Line 36, in Claim 9, after "connection of", insert --a--

Signed and Sealed this
Twentieth Day of December, 2022

Katherine Kelly Vidal
*Director of the United States Patent and Trademark Office*